US011497481B2

(12) United States Patent
Penny et al.

(10) Patent No.: US 11,497,481 B2
(45) Date of Patent: Nov. 15, 2022

(54) ELECTROMECHANICAL SURGICAL SYSTEM INCLUDING LINEARLY DRIVEN INSTRUMENT ROLL

(71) Applicant: Asensus Surgical US, Inc., Durham, NC (US)

(72) Inventors: Matthew R Penny, Holly Springs, NC (US); Nicholas J Bender, Raleigh, NC (US); Paul W Schnur, Pipersville, PA (US); Robert Henson, Raleigh, NC (US); Dale Hinman, Thurmond, NC (US); Sevan Abashian, Carrboro, NC (US)

(73) Assignee: Asensus Surgical US, Inc., Durham, NC (US)

( * ) Notice: Subject to any disclaimer, the term of this patent is extended or adjusted under 35 U.S.C. 154(b) by 0 days.

(21) Appl. No.: 16/160,960

(22) Filed: Oct. 15, 2018

(65) Prior Publication Data

US 2022/0008146 A1    Jan. 13, 2022

Related U.S. Application Data

(63) Continuation of application No. PCT/US2017/027818, filed on Apr. 14, 2017.
(Continued)

(51) Int. Cl.
*A61B 46/10* (2016.01)
*A61B 17/00* (2006.01)
(Continued)

(52) U.S. Cl.
CPC ........ *A61B 17/00234* (2013.01); *A61B 34/30* (2016.02); *A61B 34/71* (2016.02);
(Continued)

(58) Field of Classification Search
CPC ......... A61B 34/30; A61B 34/71; A61B 34/37; A61B 46/10; A61B 2017/00367;
(Continued)

(56) References Cited

U.S. PATENT DOCUMENTS 6,723,106 B1    4/2004   Charles et al.
7,608,083 B2   10/2009   Lee et al.
(Continued)

FOREIGN PATENT DOCUMENTS

CN    103329347 A    9/2013
JP    2005131173 A   5/2005
(Continued)

OTHER PUBLICATIONS

International Search Report and Written Opinion dated Jun. 29, 2017 for International Application No. PCT/US2017/027818.
(Continued)

*Primary Examiner* — Jocelin C Tanner

(57) ABSTRACT

A surgical system includes a drive unit on a support. The drive unit includes motors or other actuators and a plurality of output elements arranged such that operation of each drive unit linearly translates a corresponding one of the output elements. A surgical device has an input subsystem carried at the proximal end of the shaft. The input subsystem includes linearly translatable input elements or pistons. The input and output elements are positioned such that operation of an actuator linearly translates an output element, causing linear translation of a corresponding input element. The input elements deliver linear motion to a rotary conversion system which converts the linear motion to rotary motion and delivers the rotary motion to a shaft of the surgical device, causing axial rolling of the surgical device or its distal end effector. A sterile drape is positionable between the input elements and the output elements.

18 Claims, 27 Drawing Sheets

Related U.S. Application Data

(60) Provisional application No. 62/322,539, filed on Apr. 14, 2016, provisional application No. 62/322,585, filed on Apr. 14, 2016, provisional application No. 62/322,529, filed on Apr. 14, 2016.

(51) Int. Cl.
*A61B 34/30* (2016.01)
*A61B 34/00* (2016.01)

(52) U.S. Cl.
CPC .... *A61B 46/10* (2016.02); *A61B 2017/00327* (2013.01); *A61B 2017/00367* (2013.01); *A61B 2017/00477* (2013.01); *A61B 2017/00876* (2013.01); *A61B 2034/301* (2016.02); *A61B 2034/303* (2016.02)

(58) Field of Classification Search
CPC .......... A61B 2017/00876; A61B 2017/00477; A61B 2017/00323; A61B 2017/00327; A61B 2017/00296; A61B 2034/301; A61B 2034/303; A61B 2034/302; A61B 17/29
See application file for complete search history.

(56) References Cited

U.S. PATENT DOCUMENTS

| | | | |
|---|---|---|---|
| 7,699,855 B2 | 4/2010 | Anderson et al. | |
| 7,862,580 B2 | 1/2011 | Cooper et al. | |
| 7,886,743 B2 | 2/2011 | Cooper et al. | |
| 8,206,406 B2 | 6/2012 | Orban, III | |
| 8,333,755 B2 | 12/2012 | Cooper et al. | |
| 8,465,414 B2 | 6/2013 | Nishikawa et al. | |
| 8,491,603 B2 | 7/2013 | Yeung et al. | |
| 8,603,077 B2 | 12/2013 | Cooper et al. | |
| 8,852,208 B2 | 10/2014 | Gomez et al. | |
| 9,125,662 B2 | 9/2015 | Shelton, IV | |
| 2006/0196299 A1 | 9/2006 | Taboada et al. | |
| 2007/0135803 A1 | 6/2007 | Belson | |
| 2011/0174099 A1 | 7/2011 | Ross et al. | |
| 2012/0150154 A1 | 6/2012 | Brisson et al. | |
| 2013/0102846 A1 | 4/2013 | Sjostrom et al. | |
| 2013/0110129 A1* | 5/2013 | Reid | A61B 34/30 606/130 |
| 2014/0017665 A1 | 1/2014 | Steinman et al. | |
| 2014/0133180 A1 | 5/2014 | Sakai | |
| 2014/0135793 A1 | 5/2014 | Cooper et al. | |
| 2014/0305987 A1 | 10/2014 | Parihar et al. | |
| 2015/0150638 A1 | 6/2015 | Lohmeier et al. | |
| 2015/0173731 A1 | 6/2015 | Lohmeier et al. | |
| 2015/0173741 A1 | 6/2015 | Housman et al. | |
| 2015/0265355 A1 | 9/2015 | Prestel et al. | |

FOREIGN PATENT DOCUMENTS

| | | |
|---|---|---|
| WO | 2013159932 A1 | 10/2013 |
| WO | 2013159933 A1 | 10/2013 |
| WO | 2014005689 A2 | 1/2014 |
| WO | 2014129362 A1 | 8/2014 |
| WO | 2016057989 A2 | 4/2016 |
| WO | 2017015167 A1 | 1/2017 |

OTHER PUBLICATIONS

The Second Office Action for Chinese Application No. 201780036972.8, dated Jan. 17, 2022. (10 pages).

* cited by examiner

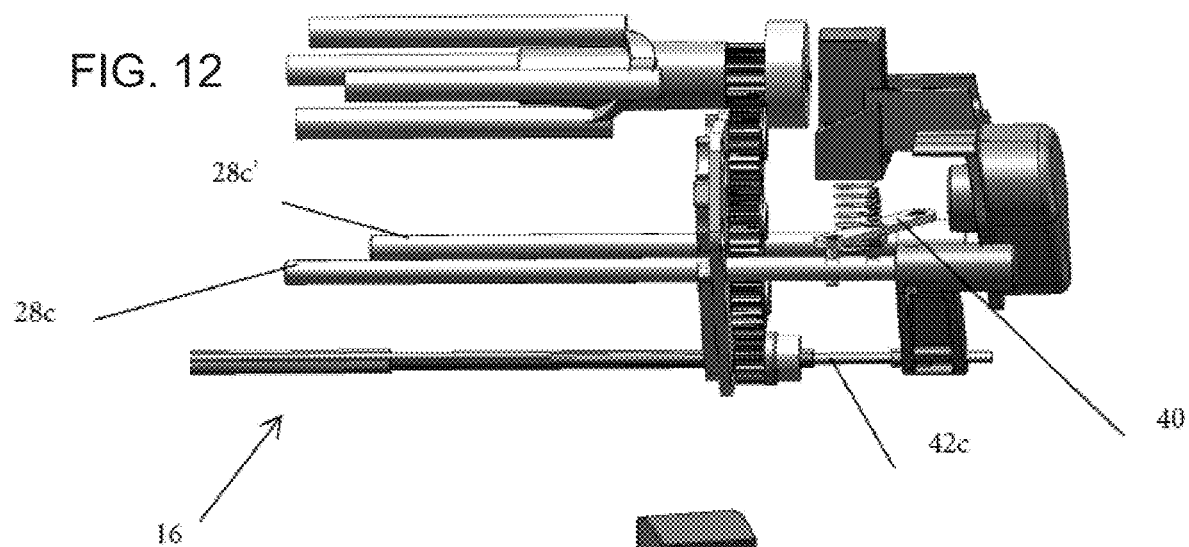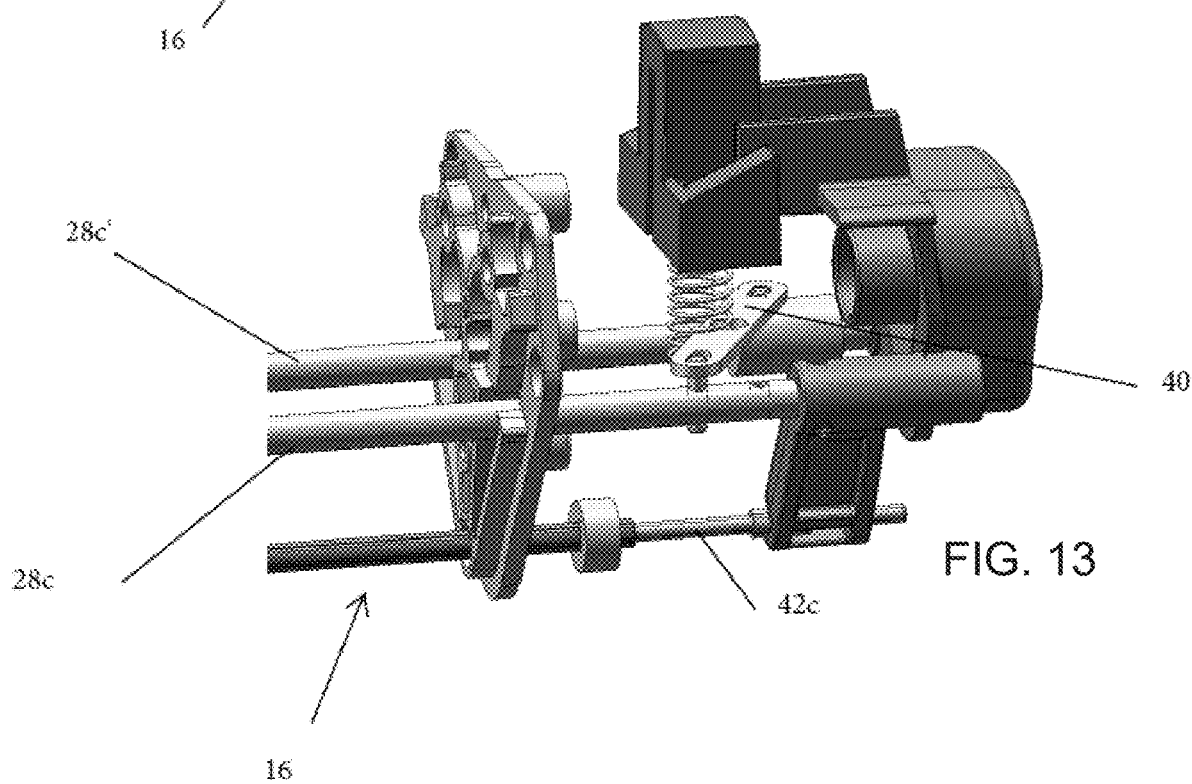

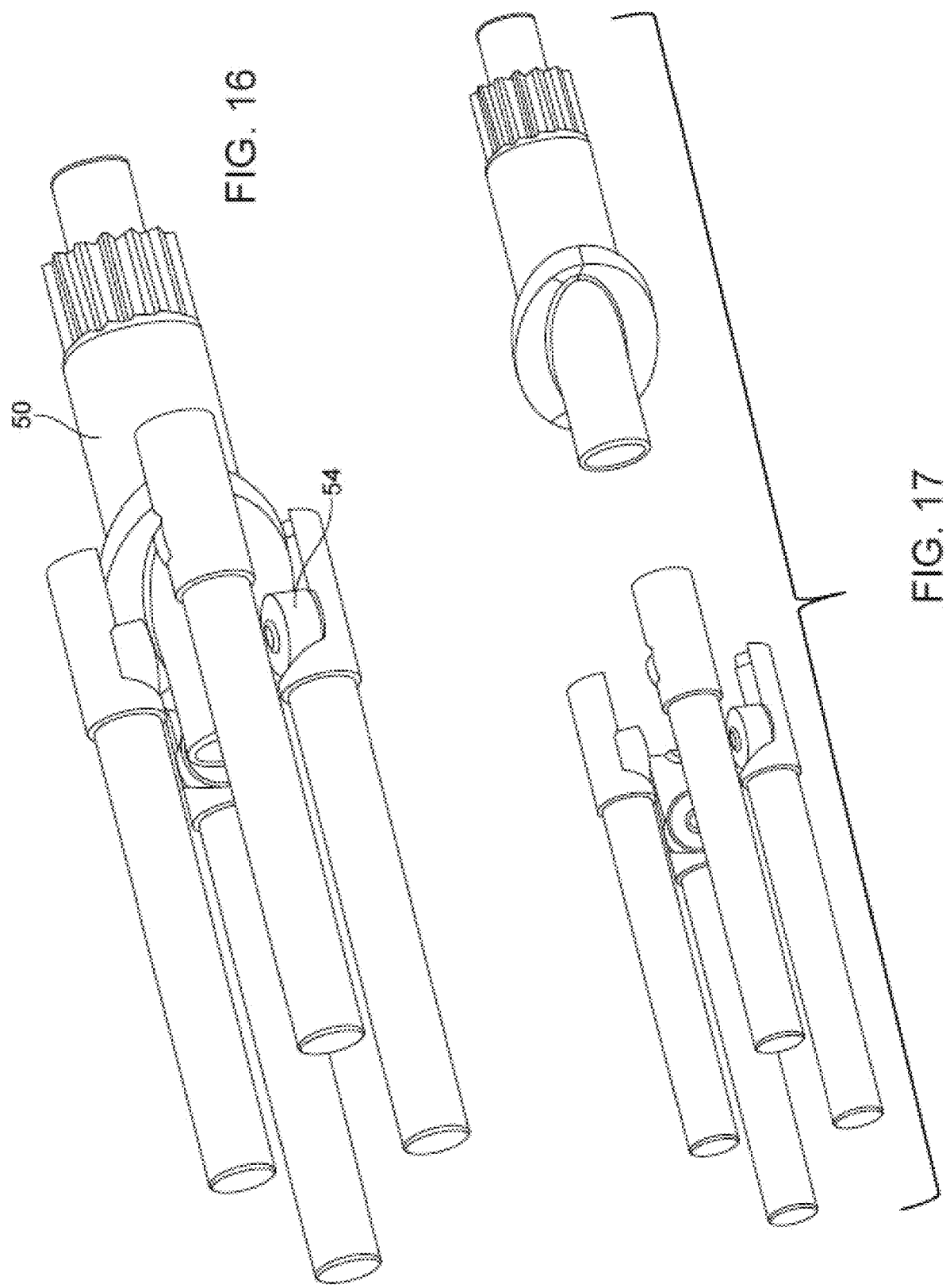

Pinion Just Disengaging from Rack.

Pinion and Rack Disengaged.

Pinion Just Clearing Rack Tooth.

Pinion Hitting Rack Tooth (Rack hasn't Moved Far Enough)

Pinion Engaging Wrong Tooth Face (Rack has Moved Back a Little)

Pinion Jams in Rack (Rack has Moved a Lot)

Pinion Tooth Disengaging from Rack, Pin (Top) on
Pinion Engaged with Y Shaped Boss on Rack.

Pinion and Rack Gear Teeth are Disengaged but Pin/Bosses are Engaged
Keeping the Rack from Being Able to Move to the Right.

Pinion Tooth on the Bottom is Starting to Engage the Rack Tooth.
The Top Pin is Disengaging from the top Boss.

Pinion Gear Still Rotating Counterclockwise but Rack is Engaged and
has Switched Directions to Travel Left to Right.

ELECTROMECHANICAL SURGICAL SYSTEM INCLUDING LINEARLY DRIVEN INSTRUMENT ROLL

This application is a continuation of PCT/US2017/27818, filed Apr. 14, 2017, which claims the benefit of U.S. Provisional Application Nos. 62/322,529, 62/322,539, and 62/322,585, each of which was filed Apr. 14, 2016. The above applications are each incorporated herein by reference.

TECHNICAL FIELD OF THE INVENTION

The present invention relates to the field of surgical systems using electromechanical drivers to effect movement of medical instruments within a body cavity.

BACKGROUND

Surgical systems used for robotically-assisted surgery or robotic surgery employ electromechanical drivers to drive movement of surgical devices within a body cavity, typically in response to signals generated when a user moves a user input device. The surgical devices may be surgical instruments having end effectors, and/or they may be steerable lumen devices adapted to receive such surgical instruments (or a combination of such surgical instruments and lumen devices). The surgical devices include actuation elements (e.g. wires, rods or cables) that, when pushed and/or pulled, cause active bending or articulation at the distal end of the surgical device, which is disposed within a patient's body. Motion produced by the electromechanical drivers is used to push and/or pull the actuation elements to produce this bending or articulation.

In such systems, it is desirable to avoid the need to sterilize components housing motors and electronics. Instead, prior art surgical systems provide the driver (which houses the motors and some electronics) as a component that may be covered with a sterile drape in the surgical procedure room. The surgical device that is to be driven by the driver is a separate, sterile, component removably mounted to the driver in a manner that allows the sterile drape to maintain a sterile barrier between the driver and the surgical device. Features are provided for transferring the mechanical output of the motors in the driver to the actuation elements in the surgical device, so that actuation of the motors causes the desired movement of the distal part of the surgical device within the patient's body cavity.

In many prior art systems, the mechanical output features of the driver take the form of rotating output elements such as shafts, disks or other elements which rotate when the motors in the driver are energized. Each such output element is rotationally coupled to a corresponding rotatable input elements on the surgical device that, when rotated, causes the pushing or pulling of the surgical device's actuation elements. To maintain the sterile boundary provided by the surgical drape that is disposed between the driver and the surgical device, the rotational motion from each rotating output element is transferred to its corresponding rotatable input element using intermediate sterile rotating pieces (e.g. rotating disks) that receive the rotational motion from the output elements of the driver and transfer the rotational motion to the input elements of the surgical device.

Commonly owned, co-pending Application PCT/US15/55098 (the '098 application), filed Oct. 12, 2015, publication WO 2016/057989, which is incorporated by reference, describes a surgical system that overcomes the challenges of the prior art systems. That application describes a system that includes a drive unit on a support. The drive unit includes motors or other actuators and a plurality of output elements arranged such that operation of each drive unit linearly translates a corresponding one of the output elements. A surgical device has actuation elements extending through an elongate shaft to a distal articulation section, and an input subsystem carried at the proximal end of the shaft. Linear translatable input elements or pistons of the input subsystem are each associated with a corresponding one of the actuation elements. The input and output elements are positioned such that operation of an actuator linearly translates an output element, causing linear translation of a corresponding input element and engagement of an actuation element. A sterile drape is positionable between the input elements and the output elements. The described system thus allows use of a sterile drape without the requirement of special adapters for transferring motion. Input devices operable by the surgeon allow a surgeon to provide input to the system for the purpose of driving the motors to move the surgical devices.

Robotic surgical procedures can be enhanced by the addition of roll capability to one or more of the surgical instruments, allowing the end effector to be rotated relative to the longitudinal axis of the instrument shaft, either by axially rolling the shaft of the instrument (with the tip thereon) or by rolling the tip of the instrument relative to the shaft (such as by rolling an internally routed shaft on which the tip is carried). The present application describes mechanisms for achieving instrument roll using a linear mechanical input, such as that provided using the linear drive system of the type described in the '098 application.

This application describes a robotic system (suitable for use in surgery) that provides an array of linear actuators against which any type of surgical or non-surgical instrument could be attached and electromechanically driven using linear inputs aligned with one or more of the linear actuators.

BRIEF DESCRIPTION OF THE DRAWINGS

FIGS. 10-14 are partially disassembled views of the proximal end of the surgical device.

FIG. 16 is a perspective view of a modified version the conversion assembly.

FIG. 17 is a partially exploded view of the assembly of FIG. 16.

DESCRIPTION

Figure 1:
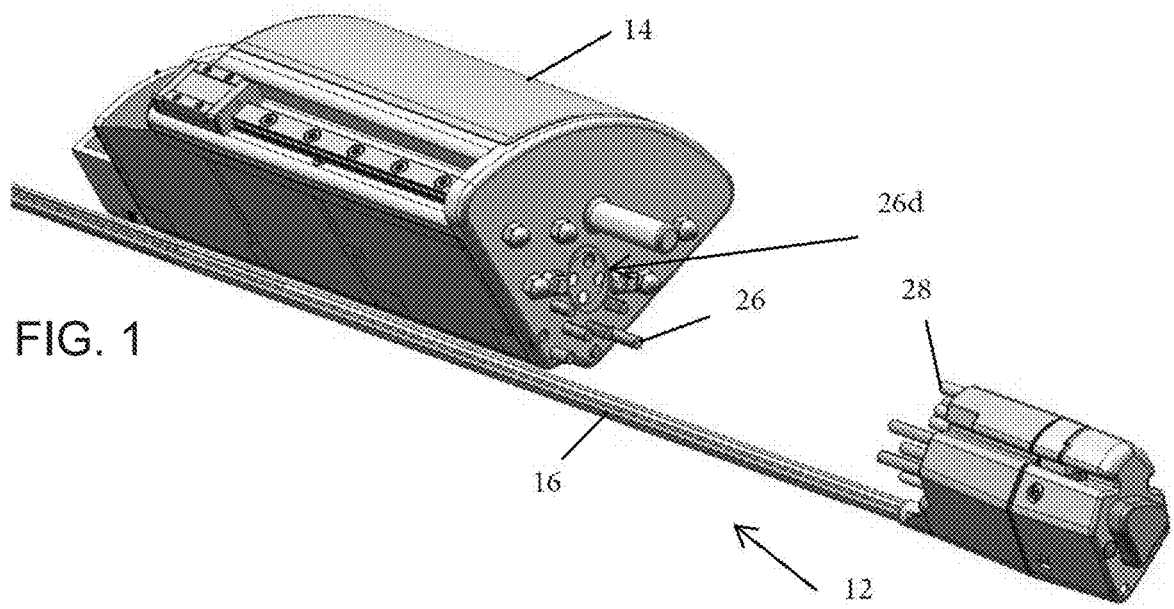
FIG. 1 is a perspective view of a first embodiment of a surgical device and motor drive assembly, showing the surgical device and motor drive separated from one another.
Figure 2:
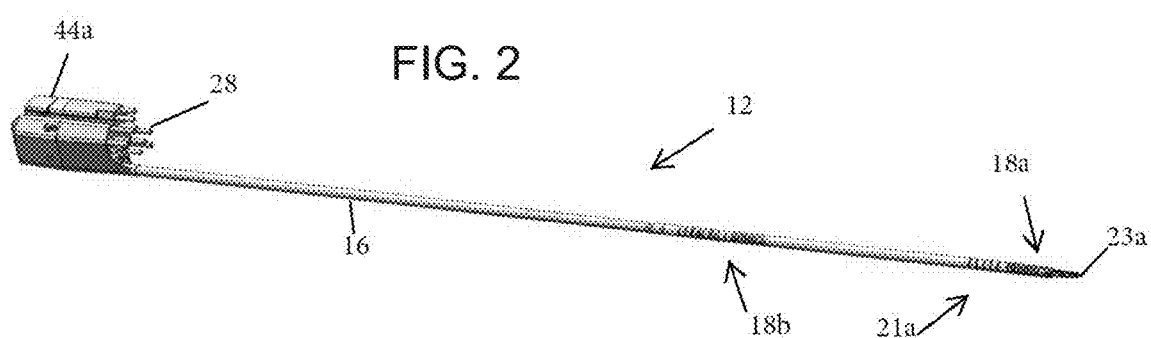
FIG. 2 is a perspective view of the surgical device of FIG. 1.

Referring to FIG. 1, an exemplary assembly 10 includes a surgical device 12 and a drive assembly such as a motor drive 14. The surgical device 12 is designed to be inserted through an incision (either directly or through a trocar or overtube) and positioned within a patient's body for use in performing surgery. It may be a surgical instrument having an end effector 23a (See FIG. 2), or it may be a steerable lumen device adapted to removably receive such surgical instruments. In some cases, there is a first surgical device in the form of a steerable lumen device driven using the disclosed principles, as well as a second surgical device in the form of a surgical instrument that is insertable through the lumen and that may also be steered, articulated, and/or actuated (e.g. jaw opening and closing) using the disclosed principles. In the present application, the illustrated embodiments show the surgical device as being a surgical instrument. Exemplary surgical devices in the form of lumen devices are found in the '098 application which is incorporated by reference. The surgical device includes actuation elements that, when pushed and/or pulled, cause active bending and/or articulation at the distal portion of the surgical device within the patient's body. The actuation elements extend through the shaft and are positioned to cause active bending/straightening of corresponding actively bendable sections, or articulation at joints or pivots, as the tension on the actuation elements is varied. The actuation elements are elongate elements (e.g. wires, rods, cables, threads, filaments etc.) having distal portions anchored to the shaft and proximal portions coupled to actuation mechanisms that vary the forces (tension or compression) on the actuation elements or the positions of the actuation elements. The actuation elements generally extend between proximal and distal directions.

Other types of actuation elements may be used (e.g. rotatable elements, inflatable elements), and the actuation elements may be used for types of motion other than bending or articulation (e.g. rotation, open/close of jaws or other elements, linear translation).

In the embodiment depicted in the drawings, the surgical device 12 includes an elongate shaft 16 having a rigid proximal portion. Towards its distal end there are one or more actively bendable or "steerable" sections 18a that bend in response to movement of the actuation elements, and/or a deployment section 18b that will articulate or bend to position the steerable section 18a laterally away from the longitudinal axis of the elongate shaft 16. The deployment section is useful during positioning of the surgical devices within the body cavity to allow for triangulation of multiple instruments towards a common operative site. It should be understood that the term "deployment" is not intended to convey that this section may only be used during deployment of the surgical device within the body. The deployment section may be comprised of one or more joints that articulate in response to movement of corresponding actuation elements, or it may be actively bendable rather than articulating. The illustrated embodiment includes both a steerable section 18a that can be steered in two degrees of freedom using steering actuation elements (e.g. three or four such elements) terminating at the distal end of the steerable section, and a steerable section 18b (as the deployment section) that is steered in at least one degree of freedom to move the distal end of the shaft laterally outward or inward in one degree of freedom using actuation elements, and which may be additionally moveable in a second degree of freedom. In another configuration, the deployment section might be configured to create an S-type bend. The numbers and combinations of actively bendable and jointed articulating sections, degrees of freedom, and actuation elements can be varied from what is shown herein without deviating from the scope of the present invention. Various designs for steerable and articulating sections of instruments are known in the prior art, and so the particular details of those sections will not be discussed here.

The motor drive 14 houses the motors whose output is used to drive the actuation elements for the steerable and/or articulating sections, as applicable. The motor drive 14 is preferably supported within the surgical procedure room using a support arm or alternate support. Multiple such support arms may be used to support multiple motor drives, allowing multiple ones of the system 10 to be used in a surgical procedure, with the surgical device shafts 16 extending through a common incision or separate incisions.

Figure 3A:
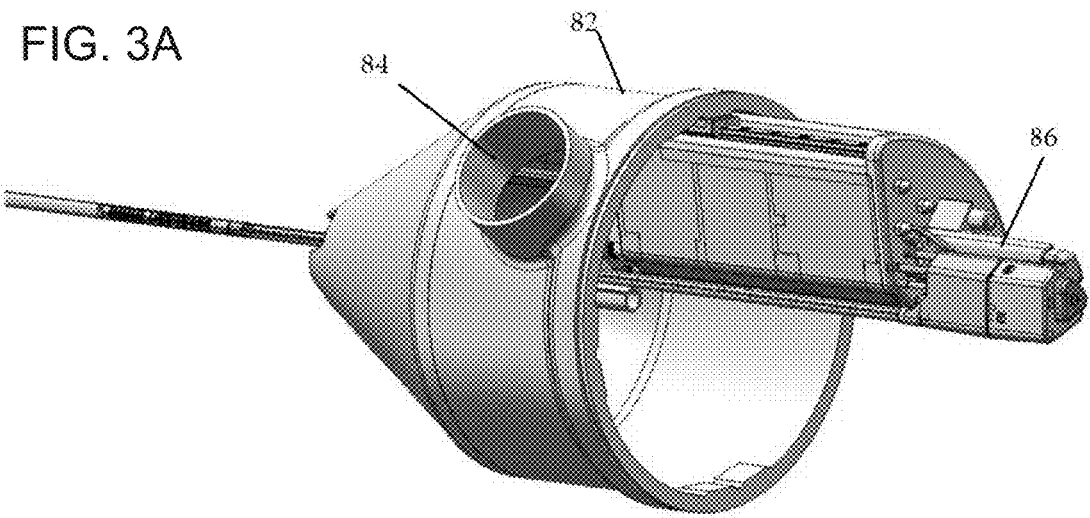
FIG. 3A shows the motor drive and instrument of FIG. 1 positioned with the input and output elements in the driving relationship and with the motor drive supported by a housing that can be supported by a support arm.

In other embodiments, the system will include two or more such motor drives 14, each having an associated surgical device 12. In such cases, a common support arm might support two or more motor drives so that two or more driven surgical devices 12 may extend into a patient through a common incision or through multiple incisions. In some cases, one of the surgical devices 12 might be a scope used to observe the procedure. In FIG. 3A, the motor drive 14 is shown mounted to a housing 82 that may be used to support a plurality of such motor drive 14 and surgical device assemblies in positions that allow the shafts 16 of the surgical devices to extend in parallel to one another through a common incision in a body cavity. One of the surgical devices in such an arrangement may be surgical scope that can be positioned and oriented (including through deployment, active bending or articulation) within the body cavity using the features described herein. A mount 84 on the housing allows the housing to be connected to a support arm. Support arms that may be used for this purpose are known in the art. One such arm is illustrated in US Publication No. 2014/0107665. In FIG. 3A, an arm 100 is shown with a housing 82 supported by it. The arm may be supported by a column that is on a base positioned on the floor of the operating room, or it might be mounted to the ceiling, the patient support table, or some other structure. This figure shows a configuration in which four motor drives 14, each with a corresponding surgical device assembly 12, are positioned on or in the housing 82, with the shafts 16 of the surgical devices positioned for insertion through an incision.

Features on the housing 82, the motor drive's housing, and/or surgical device assembly may be used to support the motor drive and surgical device assembly in the drive relationship. For example, referring again to FIG. 3A, a support member 86 may be mounted to the housing of the motor drive 14 before or after it is covered with a sterile drape, and the housing 44 of the surgical device 12 may be mounted to that support member. As described in the '098 application, the drape creates a sterile barrier between the motor drive assembly 14 and the surgical device assembly 12.

Figure 4A:
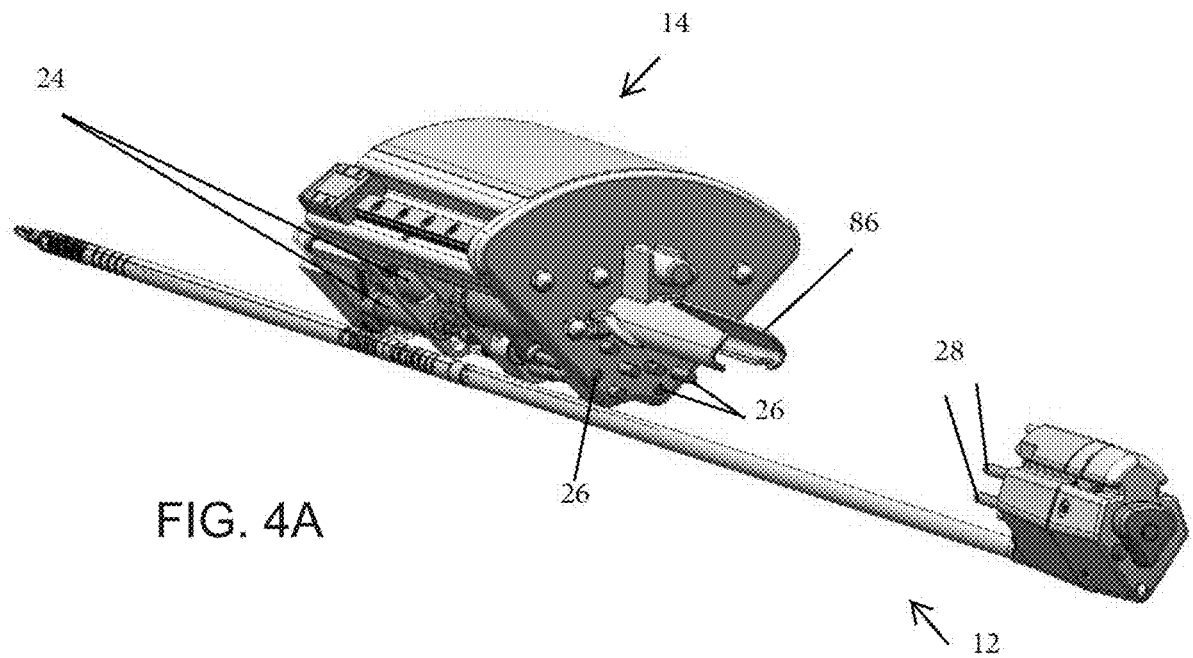
FIG. 4A is similar to FIG. 1, but shows a portion of the motor drive housing removed to show the presence of motors inside.
Figure 4B:
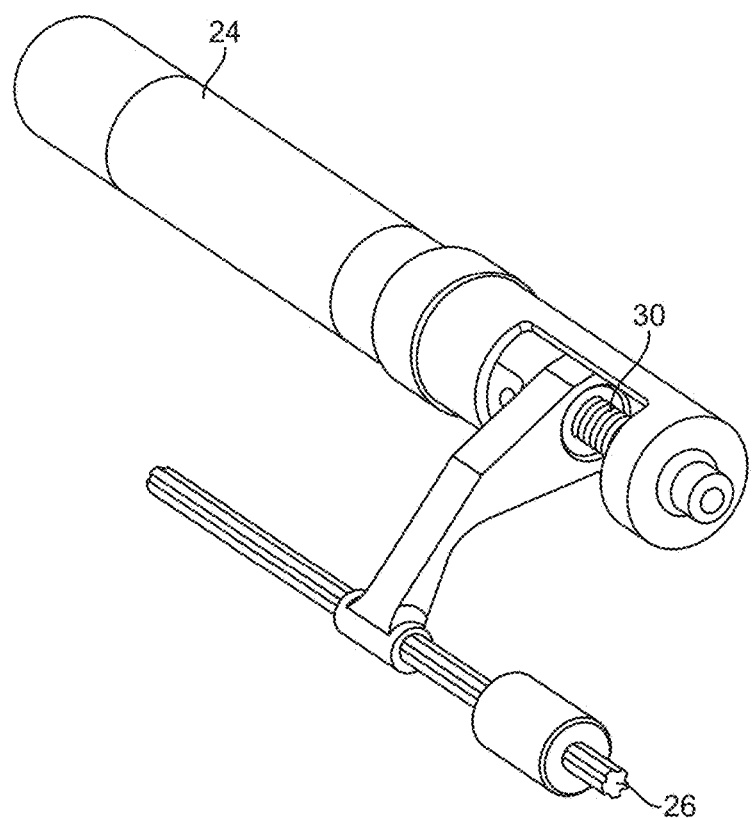
FIG. 4B shows a motor and lead screw drive associated with an output element.

FIG. 4A shows the motor drive 14 with a portion its housing removed. The surgical device 12 is shown separated from the motor drive 14. The motor drive 14 includes motors 24 and output elements 26, which in this embodiment take the form of pins or posts. When the motor drive 14 and surgical device 12 are assembled, each such output element 26 is in contact with, coupled to, or engaged with a corresponding input element 28 of the surgical device 12, or otherwise positioned to cause each input element 28 to move in accordance with its corresponding output element 26. The system may be set up so that the output elements 26 push the input elements 28 in response to motor activation, and/or so that the output elements pull the input elements 28. The embodiments described in this application focus primarily on "push" actuation, but it should be understood that these embodiments may be operated to include "pull" activation alone or in combination with push activation (as described in the '098 application), in each case without departing from the scope of the inventive concepts described here.

In most applications, a surgical drape will extend between the motor drive 14 and the surgical device 12, and will extend between the input elements 28 and the output elements 26 to prevent the sterile surgical device 12 from losing sterility due to direct contact with the motor device.

In general, the motor drive 14 is configured to transfer motion from motors 24 to linear motion of the output elements 26. For some of the output elements, lead screw drives 30 are used for this purpose. Thus, when a motor 24 is energized, its corresponding output element 26 translates linearly towards the motor to thus pull the associated input element 28 of the surgical device (FIG. 1), and/or its corresponding output element 26 translates linearly away from the motor to thus push the associated input element 28 of the surgical device.

In the illustrated embodiments, each input element and its corresponding output element translates along a common axis, but others might use nonparallel axes, different parallel axes, or other types of offset axes. The interface between the output elements 26 and the input elements 28 places the output elements 26 and input elements 28 in a drive relationship, i.e. a relationship where linear translation of the output elements 26 directly causes linear translation of the input elements 28. This interface can take a variety of forms, each of which can be achieved without penetrating the material of the drape extending between the motor drive 14 and the surgical device 12 (even though the drape is positioned between the output elements 26 and input elements 28).

The '098 application describes types of connections that can be used to allow input elements to capture, or be captured by, the corresponding output elements in a manner that does not compromise the drape extending between them, or to engage the input elements and their corresponding output elements.

Figure 7:
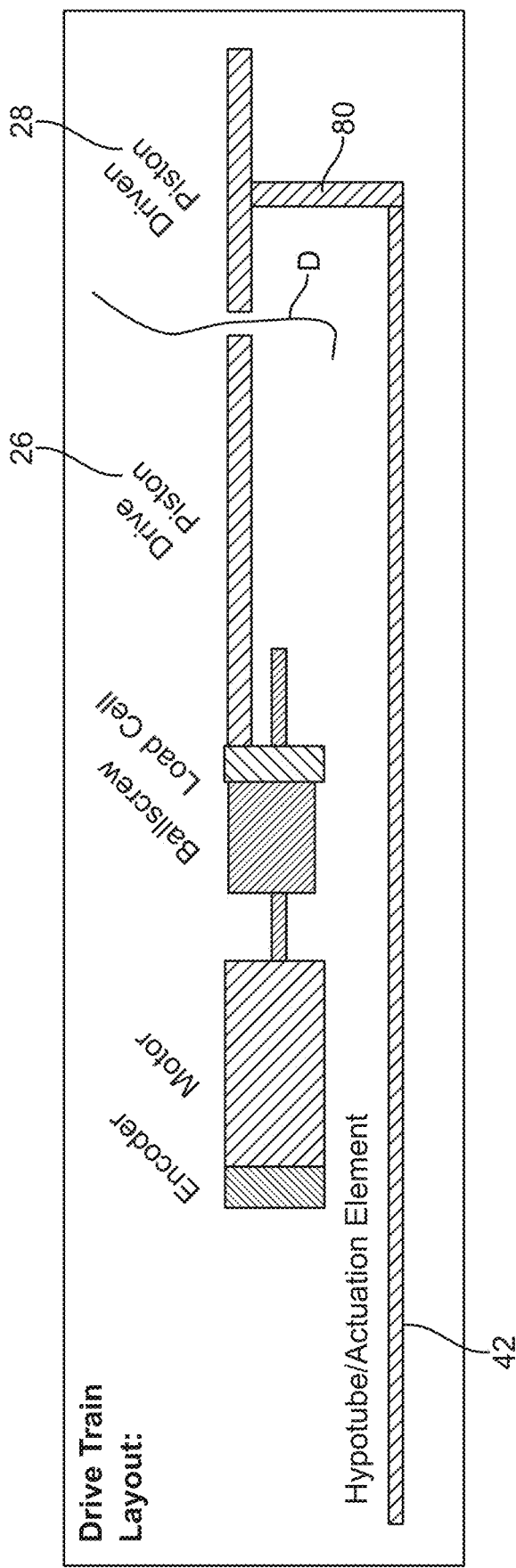
FIG. 7 schematically illustrates a drive train assembly, including a surgical device subsystem.

In the embodiment shown herein, the input elements 28 and output elements 26 are not connected to one another, but simply push against one another (with the drape D remaining between them, as illustrated schematically in FIG. 7). For example, the input and output elements might be so closely spaced that but for the drape they would be touching, or there might be a very small gap between them (with the drape disposed within that gap), The surgical device 12 includes a subsystem 38 that transfers the linear motion received from the output elements 26 of the motor drive 14 to the actuation elements 42 used for steering and/or articulation of the shaft of the surgical device 12, to any other actuation elements or assemblies used for opening and/or closing the jaws of an end effector on the distal end of the surgical device, or for axially rolling the end effector 23. Note that rolling the end effector can be carried out by axially rolling the shaft 16 supporting the end effector, or by rolling the end effector relative to the shaft 16 by rotating an inner shaft (internal to the shaft 16) on which the end effector is mounted, or by other means. The linear motion received from the output elements 26 can be transferred to the actuation elements using pivotal, linear, or rotary means (including rotary means employing pulleys).

As can be seen in the schematic of FIG. 7, each input element may be connected by a rigid link 80 to a corresponding actuation element 42 that extends within the shaft of the surgical device to an anchor point. In this embodiment, the actuation element comprises hypotube, although other types of element can be used. The hypotube extends along the shaft's length to its anchor point within the surgical device shaft 16, or only a proximal portion of the actuation element may be made of hypotube with a distal portion being made of cable, wire, filament, etc. In this embodiment, activation of the motor advances output element 26, which pushes input element 28 on the other side of the drape D.

Figure 5:
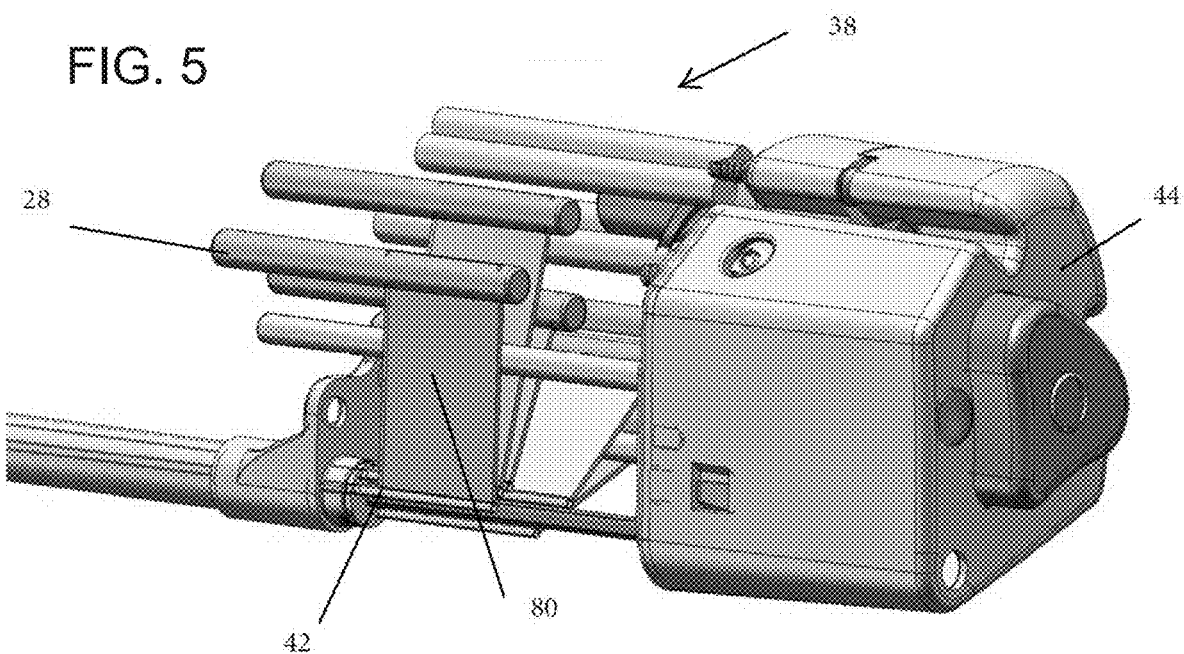
FIG. 5 shows a proximal part of a surgical device, with a portion of the housing removed to expose part of the subsystem.
Figure 6:
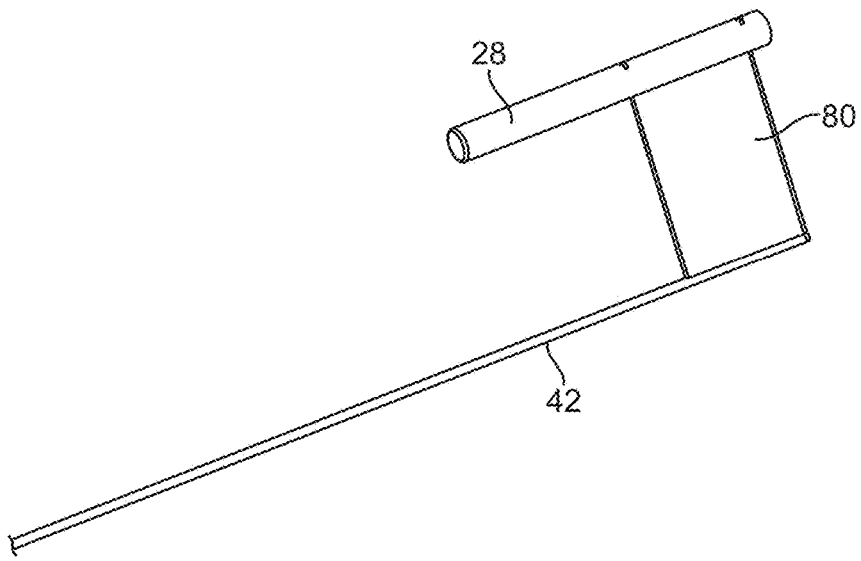
FIG. 6 shows an actuation element and input element system.

Referring to FIG. 5, subsystem 38 of the illustrated embodiment includes the input elements 28, links 80, and actuation elements 42. The subsystem 38 is enclosed within a housing 44, with the input elements 28 exposed through openings 46 in the housing where they can be acted upon by the output elements 26 of the motor drive 14.

Figure 8:
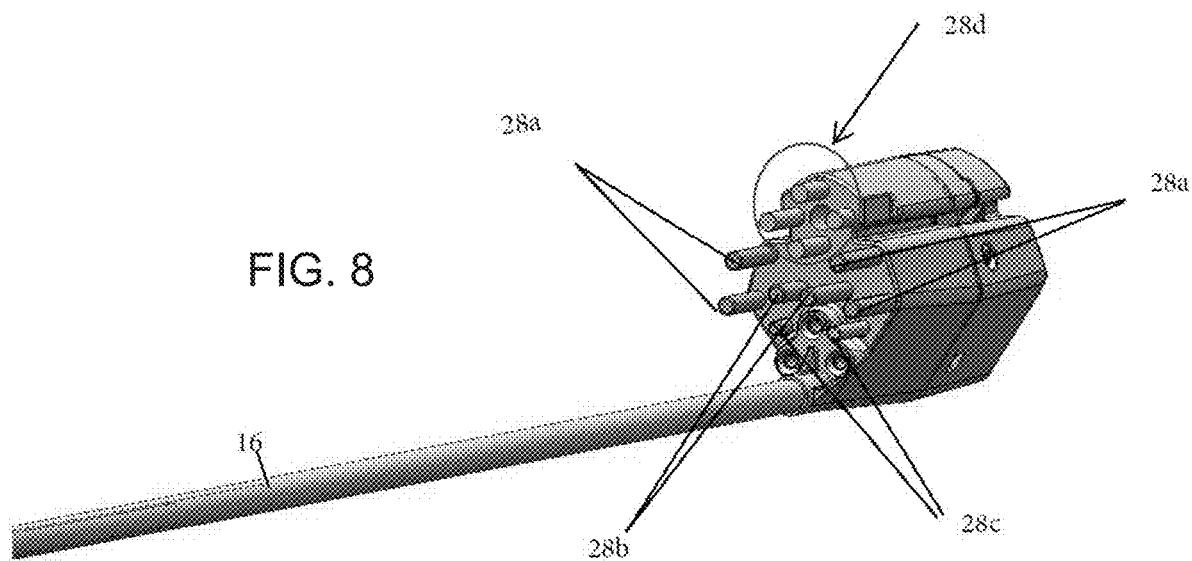
FIG. 8 is a perspective view of a proximal part of a surgical device.
Figure 9:
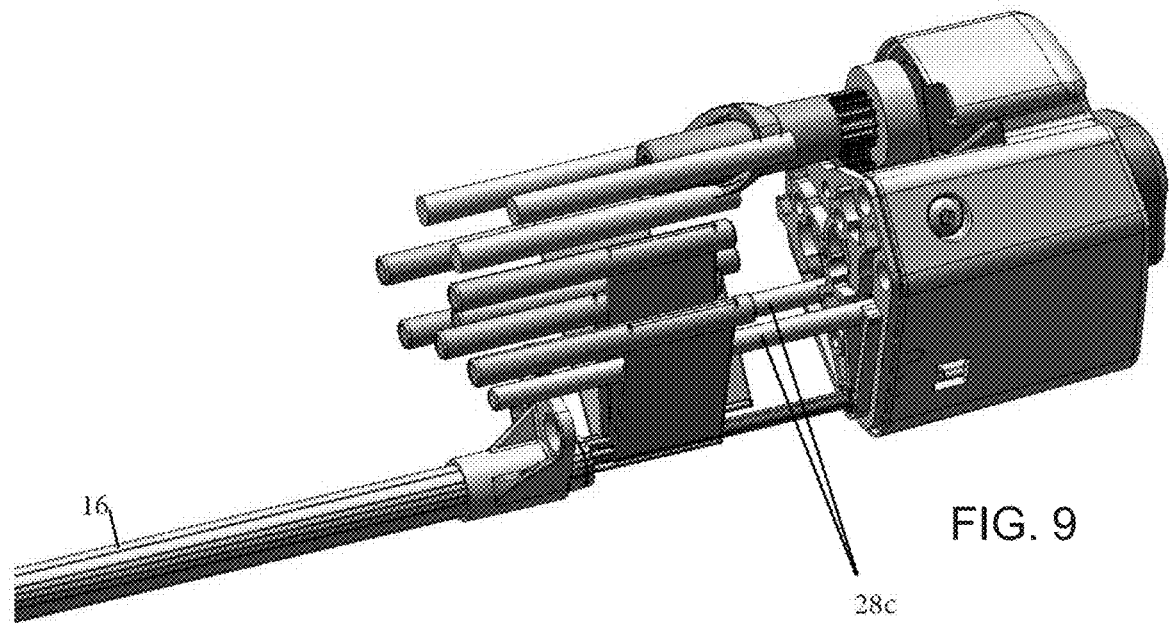
FIG. 9 shows the proximal portion of the surgical device, with a portion of the housing removed to allow the subsystem to be viewed.
Figure 10:
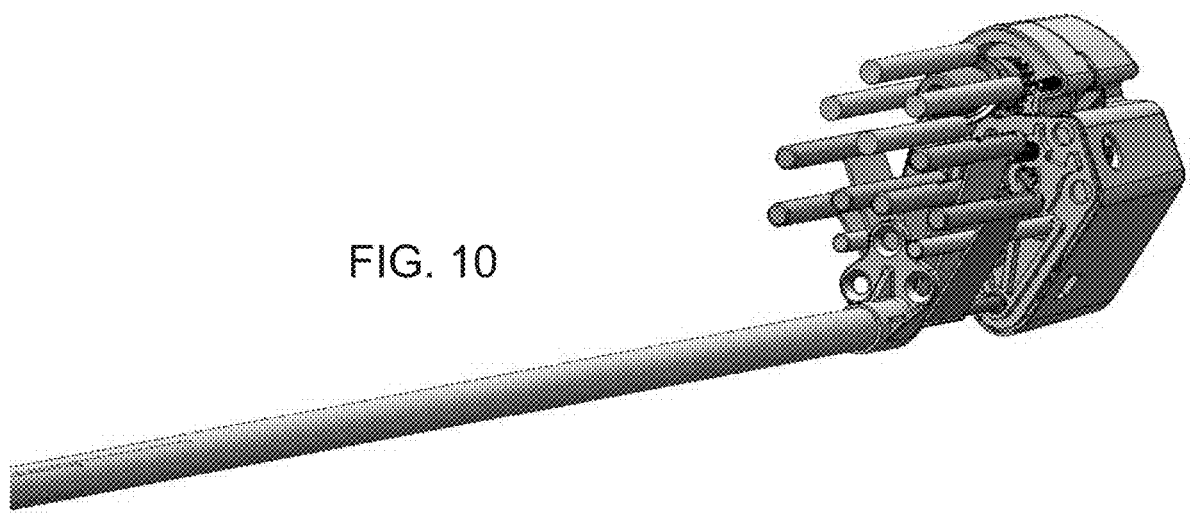
Figure 11:
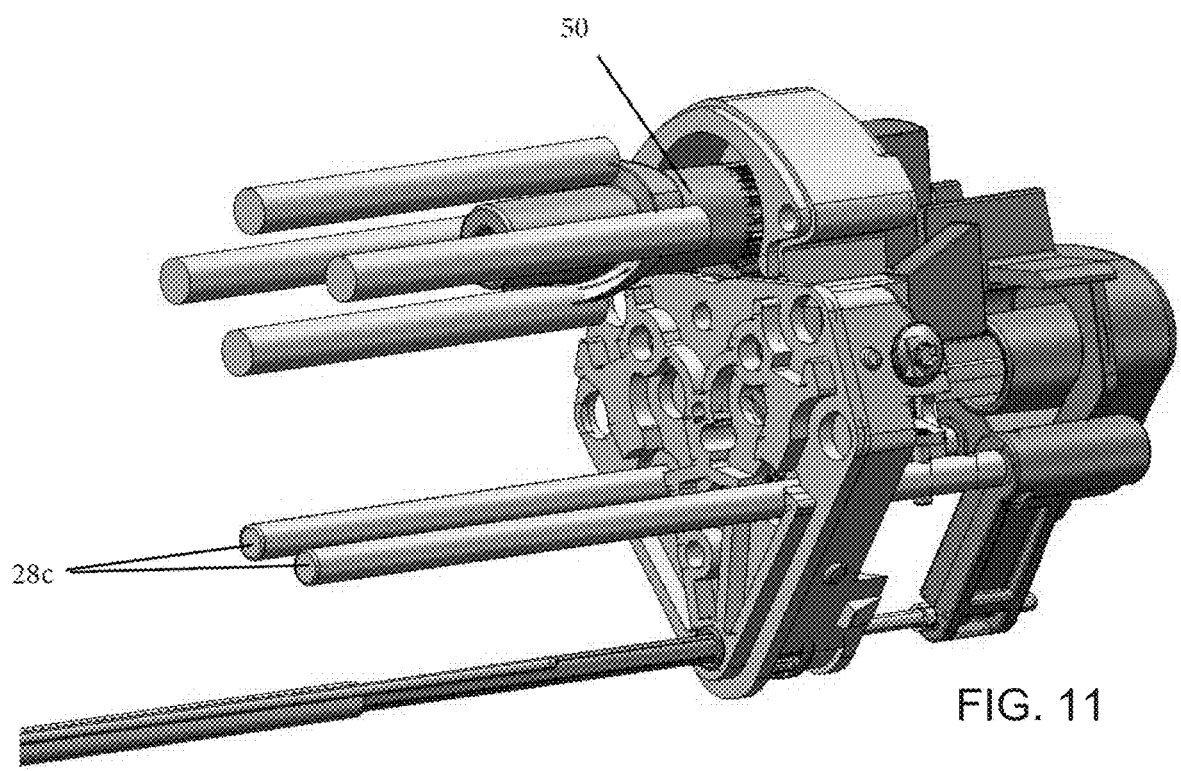
Figure 14:
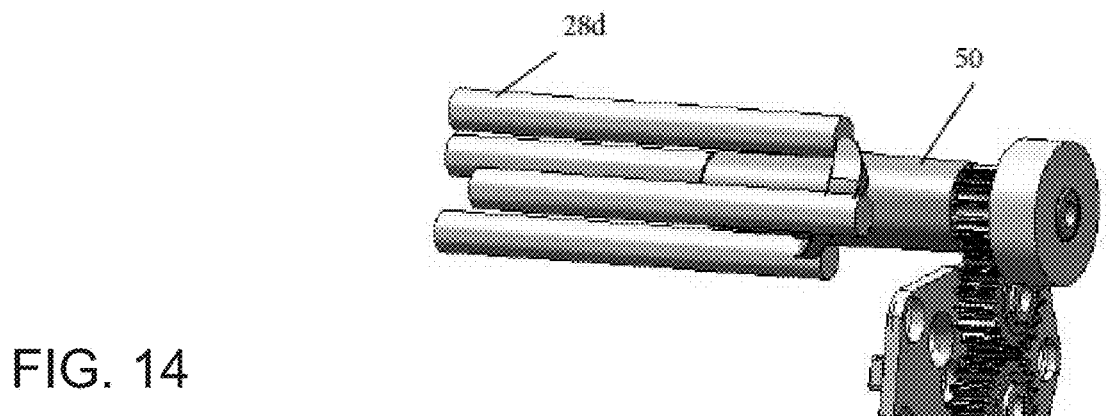
Figure 15A:
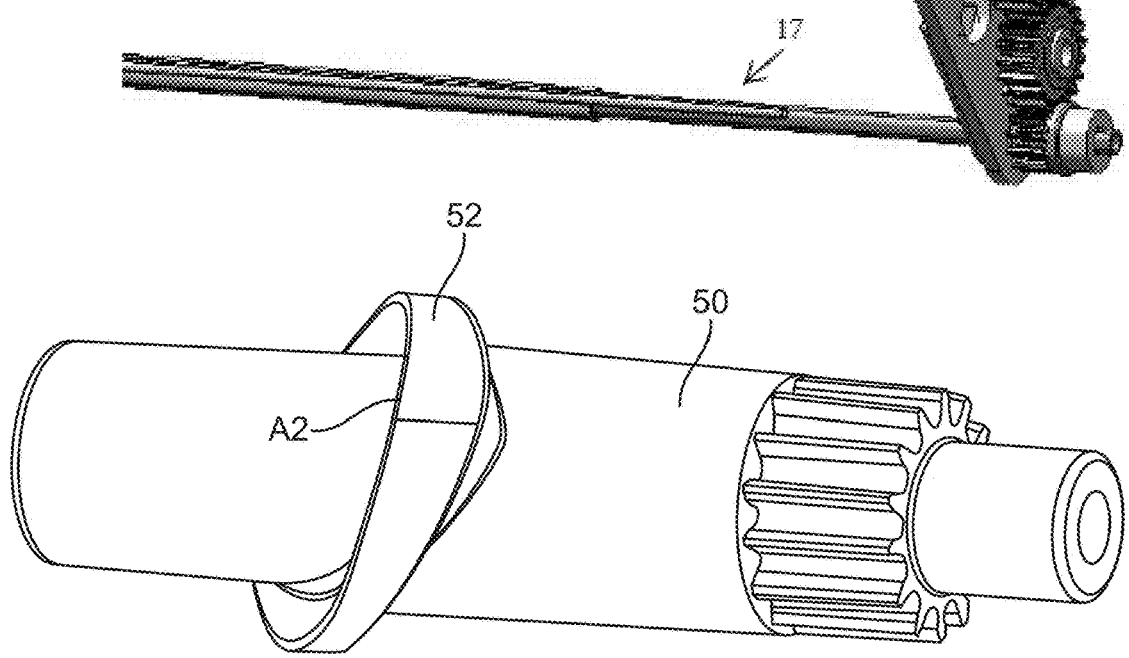
FIGS. 15A and 15B are perspective views of the rotary component of the conversion assembly.
Figure 15B:
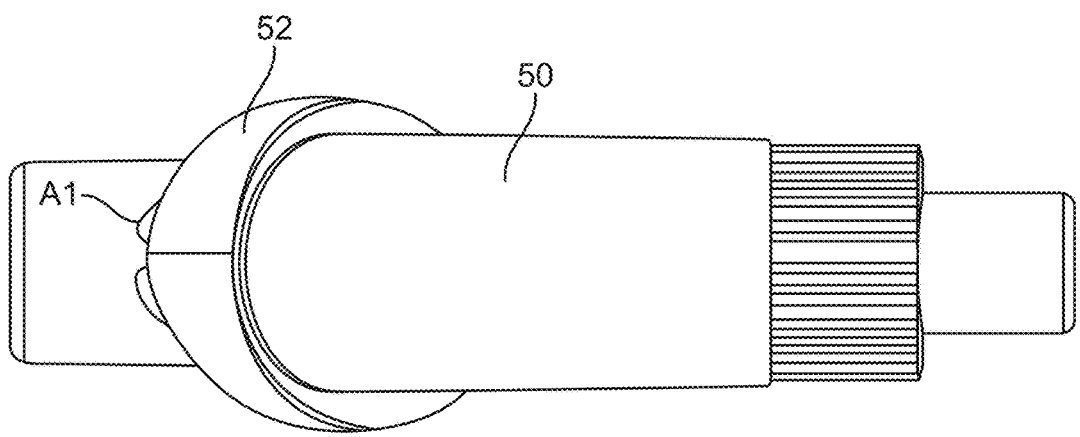

Certain of the input elements 28 are each operatively associated with a different one of the actuation elements 42. The illustrated embodiment uses six actuation elements 42 for positioning of the end effector (e.g. 4 for movement of the actively bendable section in 2 degrees of freedom and 2 for movement of the deployment section in 1 degree of freedom). Other embodiments might use as few as one actuation elements 42, while some might use more than six, depending on the degrees of freedom needed, and the elements may be distributed to uniquely control degrees of freedom in any desirable way (3 elements for 2 DOF motion, 2 elements for 2 DOF motion (if the elements are arranged to be both actively pushed and pulled, etc.) Where the surgical device 14 is a surgical instrument having jaws, an additional actuation element (or, in other embodiments, two) may be used for opening and closing of the jaws as described below Referring to FIG. 8, an embodiment of the surgical device 14 includes multiple sets of input elements 28. In this embodiment, the input elements marked 28a operate the actuation elements whose actuation results in steering of the section 18a in two degrees of freedom. Four such input elements, associated with four actuation elements, are shown, but it should be appreciated that two or three input elements and corresponding actuation elements might instead be used for steering in two degrees of freedom. The two input elements marked 28b operate the actuation elements whose actuation results in steering of the deployment section 18b in one degree of freedom. Additional input elements 28b may be added if a second degree of freedom is needed at section 18b or elsewhere along the shaft.

The input elements marked 28c, 28c' are associated with opening and closing of the jaws 23a. These input elements are part of an actuation assembly that is anchored to a proximal part of actuation element 42c as shown in FIGS. 12 and 13. The distal part of actuation element 42c is not shown in the drawings, but it is operatively connected to a clevis mechanism or other system connected to the jaws to actively open or close the jaws. Such mechanisms are well known in the art.

A pivot member 40 within the housing 44 has a first end connected to input element 28c and a second end connected to the other input element 28c'. The pivot member 40 pivots on a center axis A, such that movement of one of the input elements 28c, 28c' in one direction causes the other input element to move in the opposite direction. For example, if one of the input elements 28c, 28c' is pressed towards the housing, the pivot member 40 pushes the other input element in a direction away from the housing 44. Thus, when input element 28c is pushed (which in FIG. 13 is the direction toward the right), actuation element 42c is pulled to the right to open or close the jaws, and input 28c' moves in the opposite direction as pin 28c. When the input element 28c' is pushed to the right, the pivot member 40 pushes the input element 28c to the left, causing the actuation element 42c to move to the left, moving the jaws to the opposite configuration (from closed to open, or from open to closed). Note that in some embodiments, only the input 28c is needed. In those embodiments, the input element is actively moved (e.g. pushed) by the corresponding motor driven drive element 26 to actively open or closed the jaws as described above, but a spring 28c is used to return the input element 28c to its biased position once the force imparted to it by the corresponding drive element 26 is released.

As discussed in the '098, the control system used to control steering/articulation/deployment/jaw actuation and roll of the surgical device may receive feedback from load cells associated with each (or a plurality) of the output shafts 26 or drive pistons so as to generate signals representing the force applied to the output shafts 26 (or drive pistons), rotary encoders that determine the rotational positions of the motors, and/or other sensors positioned to detect linear displacement of components of the drive assembly. These are also schematically depicted in FIG. 7. Signals from such sensors may be used, alone or in combination, by the control system to control movement and to thus optimize movement accuracy.

Additional sensors may be positioned to sense the gap formed between output and input shafts 26, 28 or pistons, so as to detect whether the gap between corresponding input and output pistons is approaching a point where an input piston might become too far out of the range of the output piston to be controlled by the output piston.

Figure 3B:
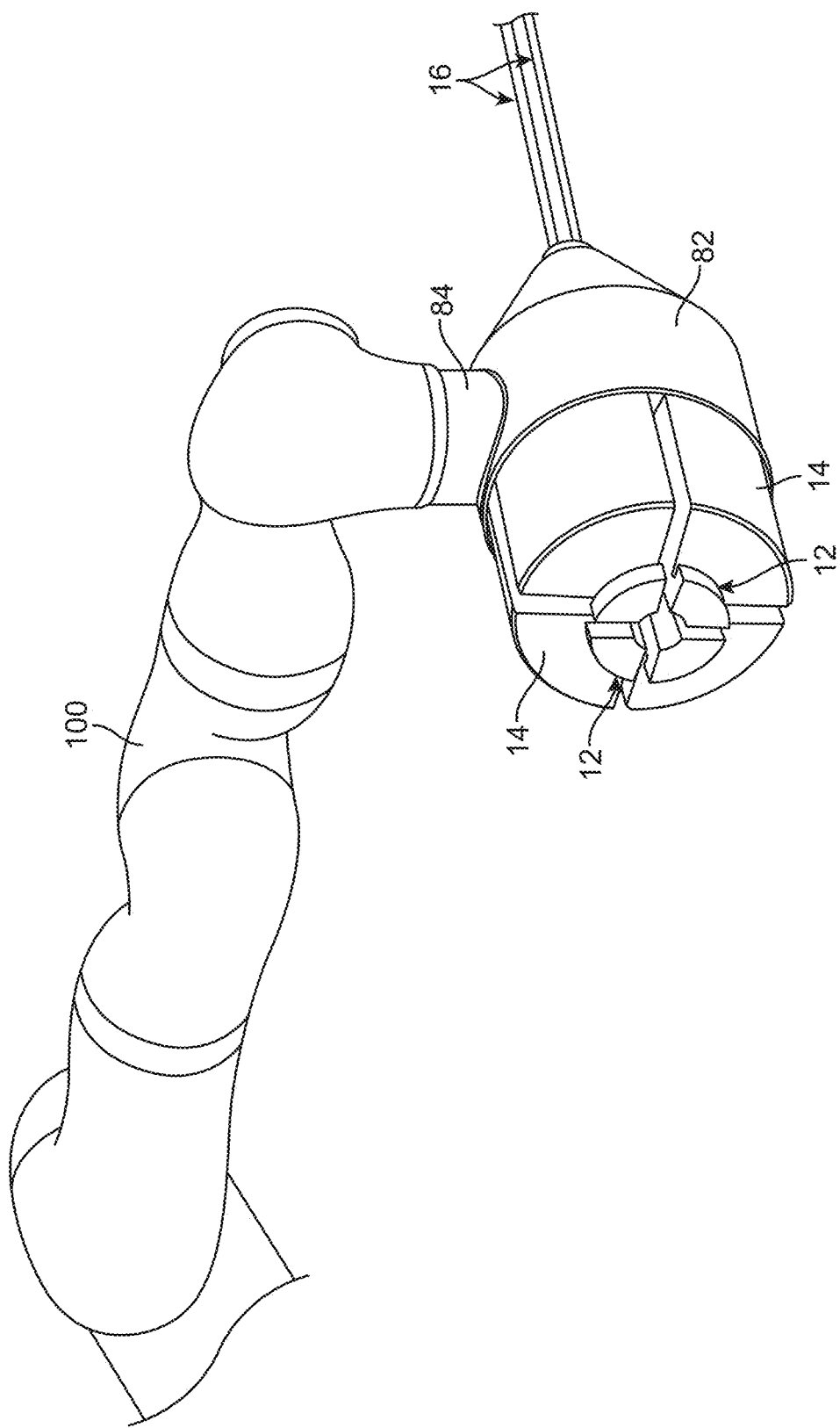
FIG. 3B shows the housing of FIG. 3A mounted to an arm, with four motor drives and four surgical devices disposed in the housing.

When the motor drive 14 and surgical instrument are placed in the drive relationship shown in FIG. 3, the input and output elements are positioned on opposite sides of the drape as shown in FIG. 7. When a motor is energized to advance an output element axially towards its corresponding input element, it pushes the input element towards the surgical device housing, causing the actuation element that is coupled to that input element to be pulled.

By way of example, consider a surgical device where the actuation elements responsible for active bending of the shaft are anchored at four locations spaced 90 degrees apart. To bend the shaft in an upward direction, a first motor might be energized to cause a corresponding first input element 28 to be pushed, resulting in the pulling of the associated first actuation element and causing the shaft to bend upwardly. To then bend the shaft downwardly, a second motor is energized to cause another, second, input element 28 to be pushed, resulting in the pulling of a second actuation element anchored 180 degrees from the first actuation element, causing the shaft to bend downwardly. As the shaft moves between the upward and downward configurations, the first input element 28 moves outwardly as a result of the change in shape of the shaft 16, and the first motor is simultaneously energized to retract the first output element 26 in a corresponding amount.

Other configurations using, for example, three actuation elements for active bending of the shaft will push the appropriate combinations of input elements 28 to achieve the desired movement.

Note that while this application shows exemplary subsystems that may be used to perform this function, alternative subsystems can be used without deviating from the scope of the invention.

The motor drive is mounted, or mountable, to a support such as a support arm of the type used for surgical systems. Mounting may be direct or via an intermediate structure. The surgical device is mounted to the support, either directly or by way of a connection to the motor drive housing or to another structure between the surgical device and the support, so that the relative positions of the motor drive housing and the surgical device (e.g. the rigid proximal portion of the shaft 16, or the housing 44) remain fixed during the surgical procedure. This maintains the input and output shafts in the drive relationship through the procedure.

A draping system for use in covering the motor device 14 might include features that accommodate the (push or pull) movement at the interface between the output elements 26 and input elements 28 without tearing the drape. Such features might include a plurality of pre-formed bellows or pockets, each positioned over one of the output elements 26, or they might include regions of material that are more elastic than the surrounding drape material. Alternatively, the drape can be provided without any such features if the elasticity of the drape is sufficient for relative movement of the output elements without perforating the drape. Alternative drape designs might include mechanical features attached to the drape to assist in the coupling of motion between output elements 26 and the input elements 28.

Assemblies for Roll Motion of Surgical Device

It is desirable in surgery to be able to rotate the shaft of the surgical device, or the instrument tip, relative to the longitudinal axis of the shaft. This section describes various embodiments of linear to rotary conversion assemblies that may be used to convert linear motion transmitted by the motor drive across the sterile barrier/drape into rotary motion of a feature (be it a pulley, gear, cam, belt drive, etc.) where it can be used to drive roll of the surgical device or end effector. These embodiments allow the rotary motion to be reversible, meaning that it can be driven in both clockwise and counterclockwise directions. In some embodiments, the rotary motion can also be continuous.

Referring again to FIG. 8, the input elements identified as 28d are used to effect axial rolling of the end effector 23a. This may be achieved by rolling the shaft 16 itself, or, as illustrated, by rolling an internal shaft 17 that extends through the shaft 16 and that supports the end effector 23a. Input elements 28d are positioned on the surgical device to interface with a central rotary component 50. Rotary component 50 has a cam surface 52 formed of an externally located shelf as shown, or an internally cut cam path. In the embodiment shown, the cam surface is a continuous curved surface encircling the shaft and having a first apex section and a second apex section, the first apex section being closer to the free end (the end extending in the direction of the end effector) than the second apex end. The first and second apex sections may be separated 180 degrees around the shaft as shown.

The input elements 28d interface with the cam path/shelf such that when one input element translates forward, it causes rotation of the rotary component in one direction and forces translation of the other input elements 28d according to the shape of the cam surface 52. Depending on which input element is being actively driven (by its corresponding one of the drive elements 26), the direction of rotation can be reversed at any time. The motion can also be continuous if the sequence in which the pins are pushed by their corresponding drive elements 26 continues in the same direction for multiple rotations.

The interface between the input elements 28d and the rotary component 50 may also include rolling members 54 as shown in FIGS. 16 and 17.

Referring again to FIG. 1, the drive elements 26d for driving the roll motion extend from the motor drive housing in the circled region marked 26d. As with the other drive elements, each of these drive elements 26d is in contact with, coupled to, or engaged with a corresponding input element 28d, or otherwise positioned to cause each input element 28d to move in accordance with its corresponding output element 26d. The motor drive 14 may include separate drive motors for each of the drive elements 26d, or gears may be used to allow two or more drive elements to be driven by a common motor. In one configuration, a motor may be configured to drive a rotary component similar to rotary component 50, and the drive elements 26d may be driven by the rotary component 50 in a manner similar to the way in which the input elements 28d drive the rotary component 50.

Although the drawings show the use of four input elements 28d, three input elements, or more than four input elements, may instead be used. If the input elements and drive elements are configured so that the drive elements can both push and pull the input elements 28d, two input elements 28d can be used.

Figure 18:
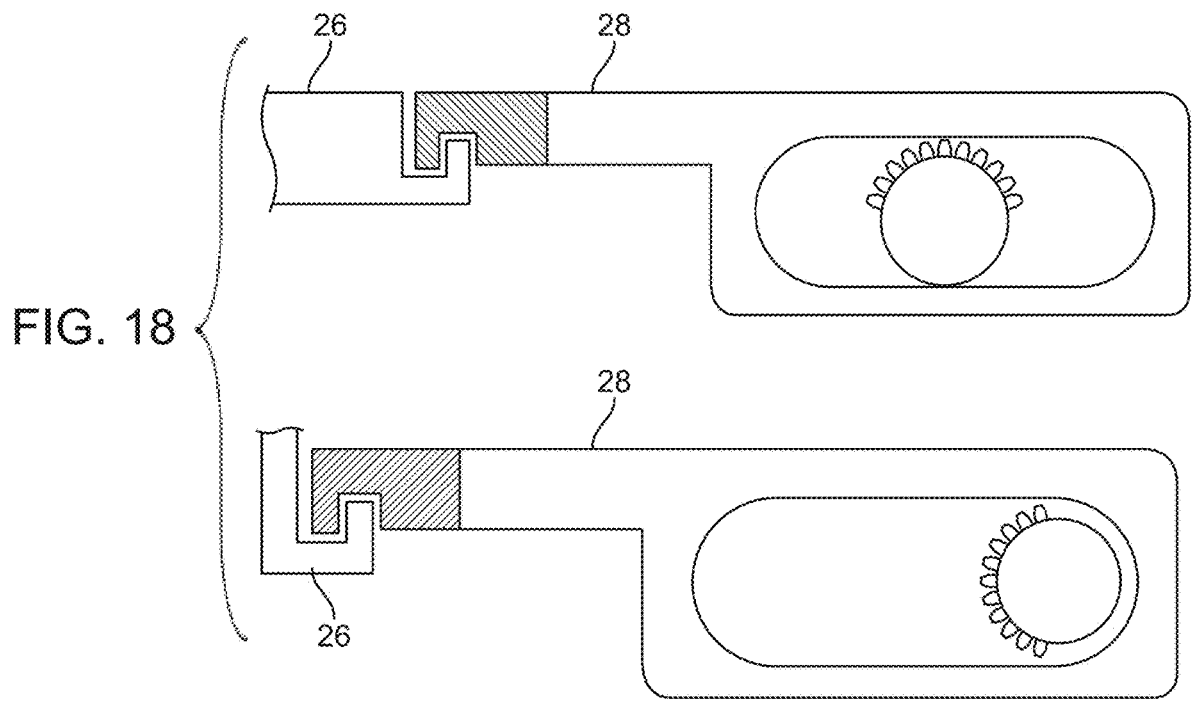
FIG. 18 shows output elements engaged with input elements of an alternative linear to rotary conversion assembly.

FIG. 18 illustrates an alternative embodiment of an assembly for converting the linear input transferred from the drive elements 26 to the input elements 28 into rotation for rolling the surgical device or instrument tip. Is this embodiment, the rotation created can be continuous and reversible, using linear translation at the drape interface of only two pins/pistons. This concept differs from the above-described concept in that this concept is designed for a system where the drive elements both push and pull the input elements at the drape. Engagement between the drive elements and input elements may be carried out using overlapping mechanical features such as the hook features shown in FIG. 18, or by using magnetic engagement to resist pulling apart, or other features, including those described in the '098.

Figure 19:
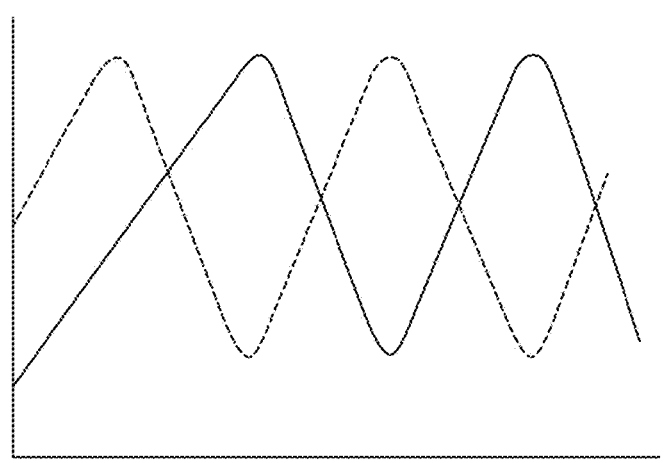
FIG. 19 graphically depicts motion of the input elements of the assembly of FIG. 18 over time.
Figure 20A:
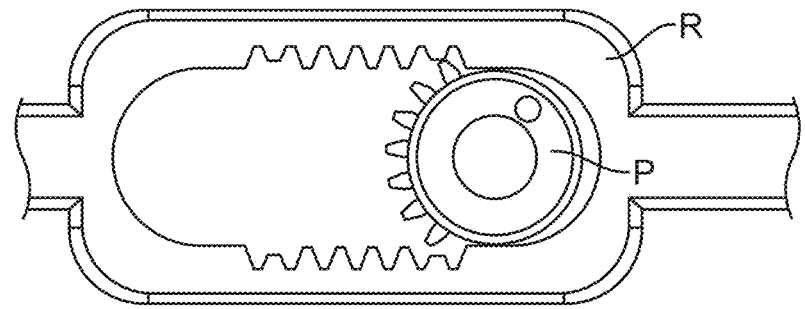
FIGS. 20A-20F are a sequence of drawings illustrating motion of a prior art rack and pinion assembly.
Figure 20B:
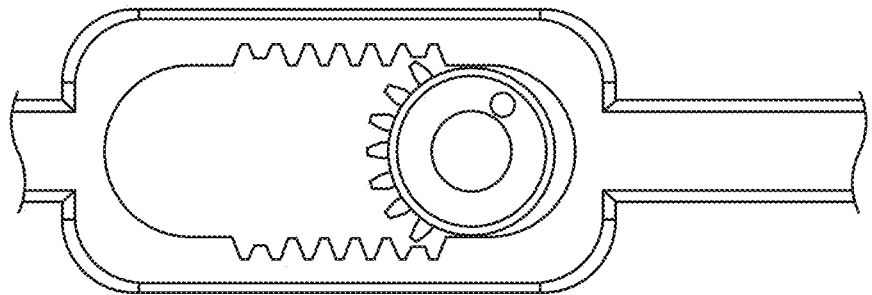
Figure 20C:
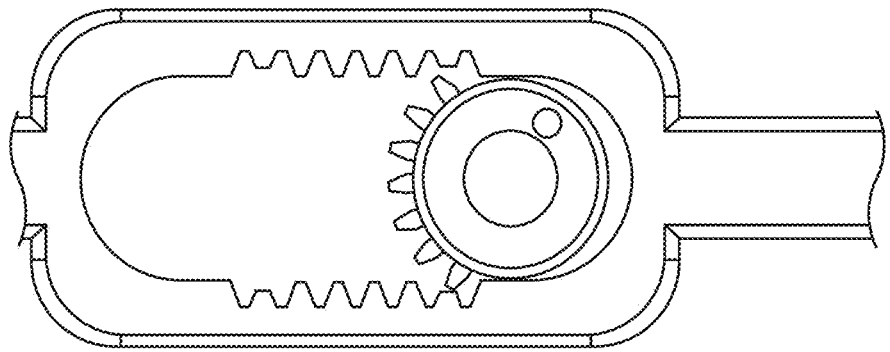
Figure 20D:
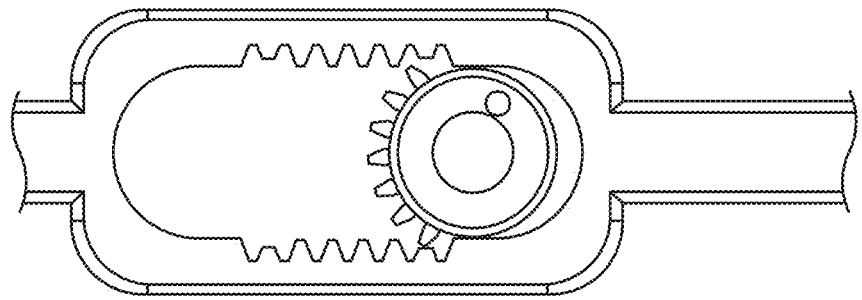
Figure 20E:
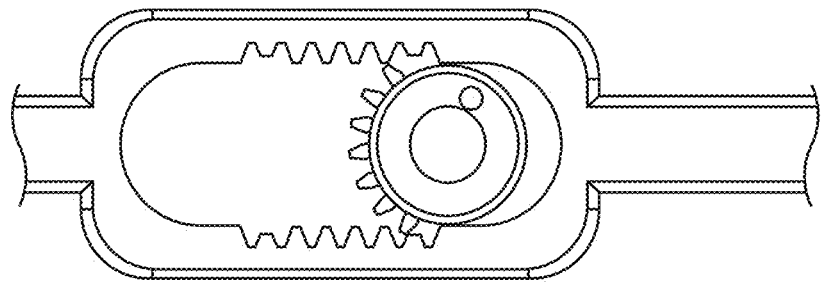
Figure 20F:
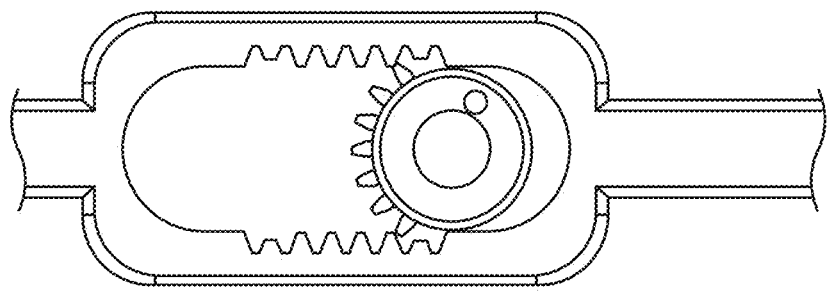

The linear inputs are connected to one another in a way that they are operating out of phase by 90 degrees. Their motion over time is depicted in the graph shown in FIG. 19. In this configuration, one input element can be pushed or pulled while the other is at its indeterminate locations. This could be done with the reciprocating rack and pinion roll mechanism as described in connection with the third embodiment, or with a simple piston/crank mechanism. This embodiment is advantageous in that it makes use of two linear translating inputs through a drape to drive continuous and reversible roll. This would reduce the number of required motors for rolling.

A third embodiment for converting the input linear translation into axial roll of the surgical instrument provides continuous, reversible rotation of a shaft. It is described in the context of a system where the output elements only push the input elements, but it can also be used in one where both pulling and pushing are used. The mechanism consists of a set of rack and pinions designed so that the rack reciprocates with a constant rotational input from the pinion. This motion can be reversed (i.e. the instantaneous direction of the rack) by reversing the pinion rotation direction. The pinion can also be driven by the racks so that one rack/pinion set can drive a matching rack pinion set. The advantage of this system over other methods of converting rotational motion to linear motion is that while the rack/pinion are engaged the mechanical advantage is constant. This will reduce (or eliminate) torque ripple in the rotating shaft.

Existing reciprocating rack and pinion mechanisms suffer from a problem in which, at the end of the rack travel, the pinion is (for a moment) disengaged from the rack entirely. In fact it is a requirement of the design that there is a moment where no gear tooth is engaged with a rack tooth and the pinion rotates freely until it engages a tooth on the opposing rack. Without this clearance the mechanism would bind as the rack tries to switch directions. This enables the mechanism to function but causes problems if there is any impediment to the rack motion at the inflection point. If the rack is not allowed to move freely (i.e. there is some friction or a force keeping the rack from traveling freely) the mechanism will jam or skip a tooth in which case it will jam the next time the rack reaches the end of travel.

FIGS. 20A through 20F illustrate the various states described above. In these drawings, the pinion P is rotating counterclockwise and the rack R is traveling right to left.

Figure 21A:
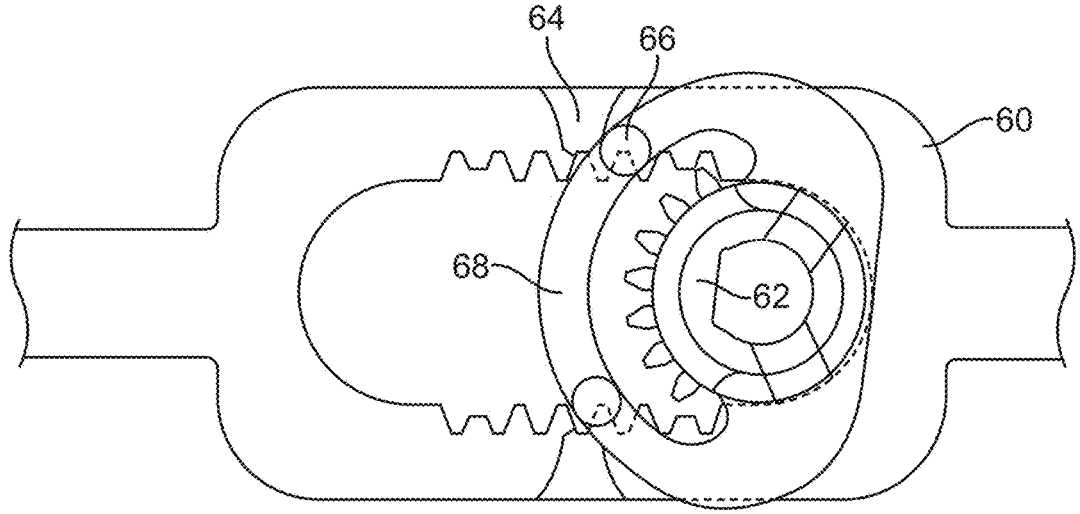
FIGS. 21A-21D are a sequence of drawings illustrating motion of a modified rack and pinion assembly suitable for use as a linear-to-rotary and or rotary-to-linear conversion assembly.
Figure 21B:
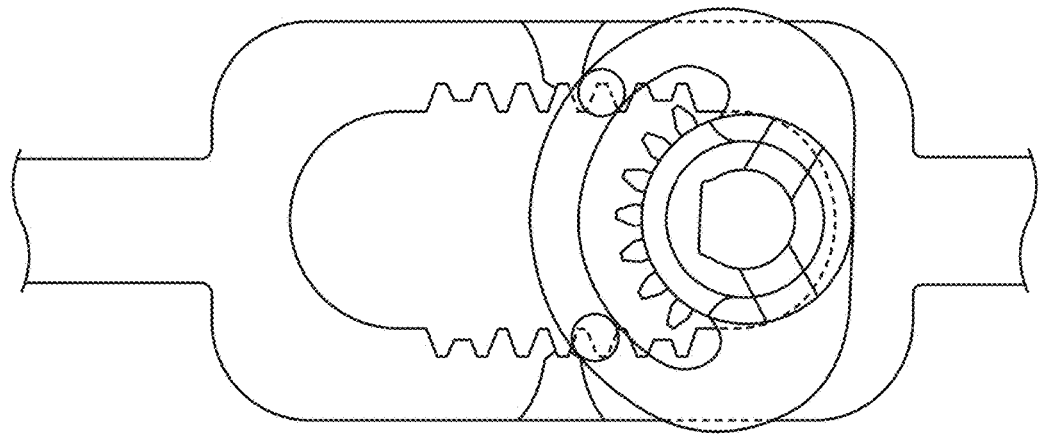
Figure 21C:
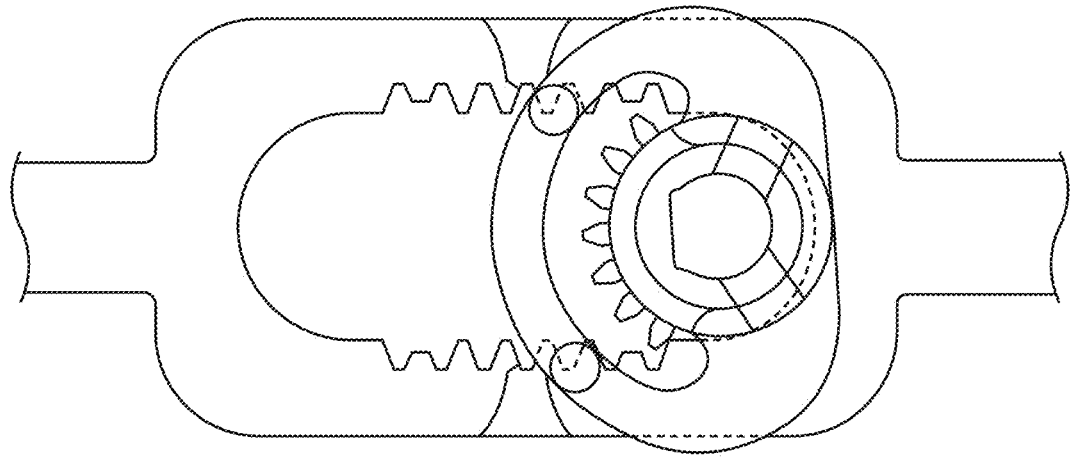
Figure 21D:
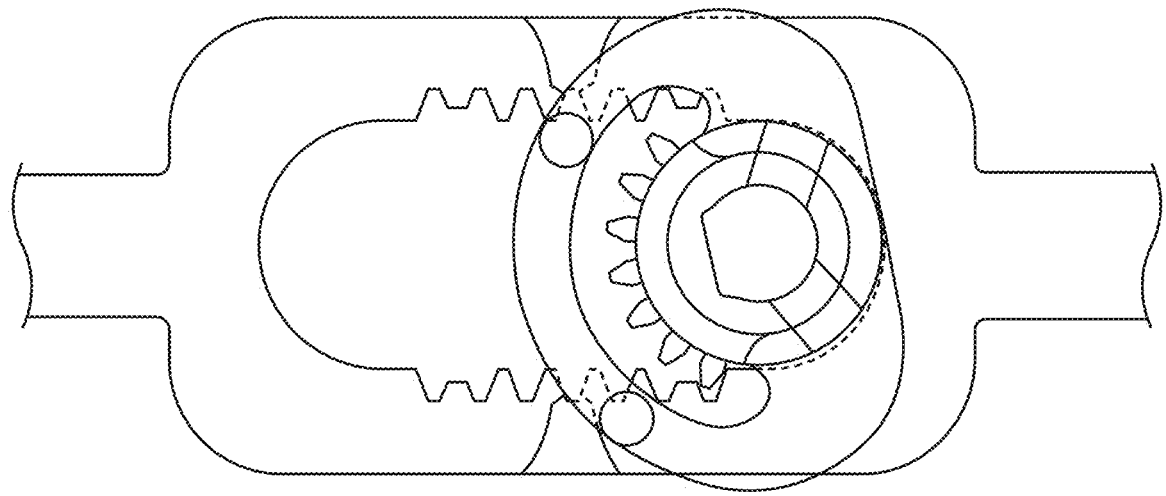
Figure 22A:
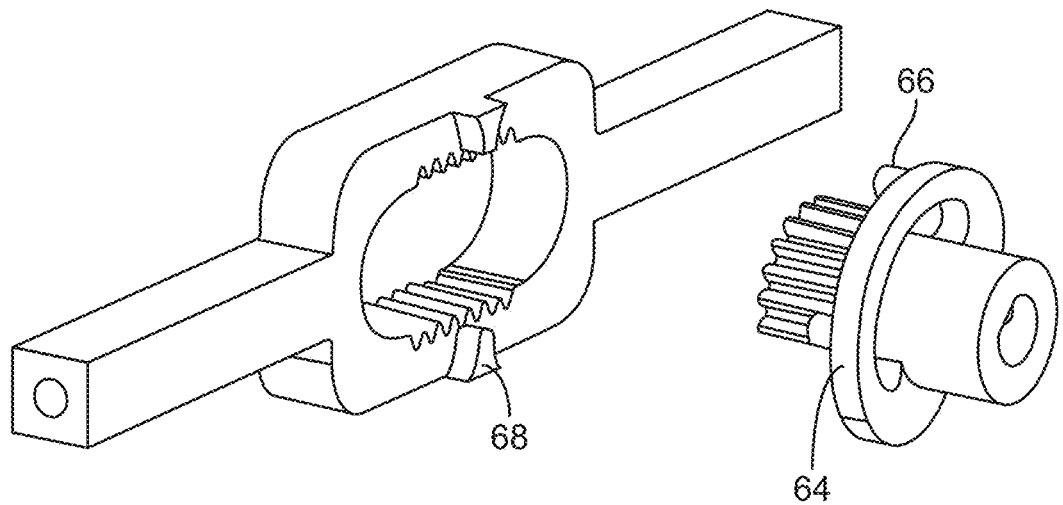
FIGS. 22A and 22B are exploded views of the assembly of FIGS. 21A-21D.
Figure 22B:
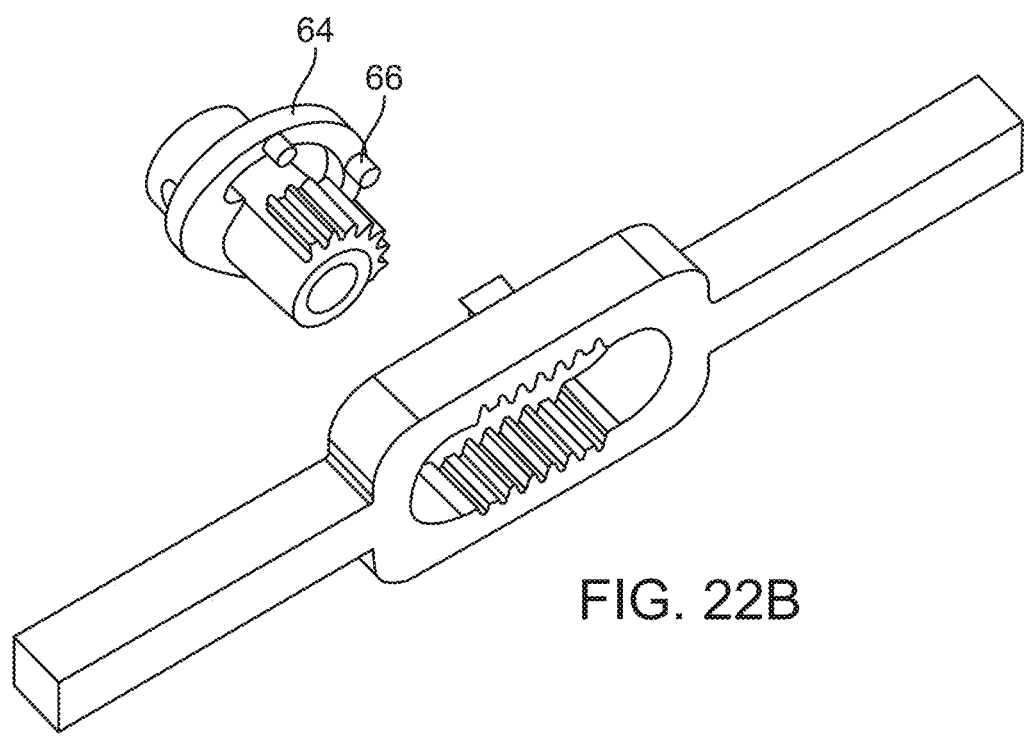

The third embodiment makes use of a rack and pinion in the instrument assembly for converting translational motion imparted to the rack into rotational motion of the pinion P, but modifies the rack and pinion configuration to overcome the difficulties described with reference to FIGS. 20A-20F. In this embodiment, in order to keep the rack 60 and pinion 62 from binding if force is applied to the rack when it is switching directions, a secondary cam/follower arrangement is added. One example of a cam/follower arrangement is shown in FIGS. 21A, 22A and 22B. The arrangement can be a single cam/follower or a combination of two as shown. Referring to FIGS. 21A, 22A and 22B, the rack 60 includes shaped bosses 64, and the pinion 62 includes pins 66 on an arcuate member 68 spaced apart from the teeth of the pinion 62. The pin 66 on the pinion gear engages the boss 64 on the rack and continues to push the rack after the pinion gear tooth has disengaged from the rack. FIGS. 21A-21D show the exemplary pin/boss configuration in the same states as described with respect to FIGS. 20A-20F. In the drawings, the pinion is rotating counterclockwise and the rack is moving right to left.

Figure 23A:
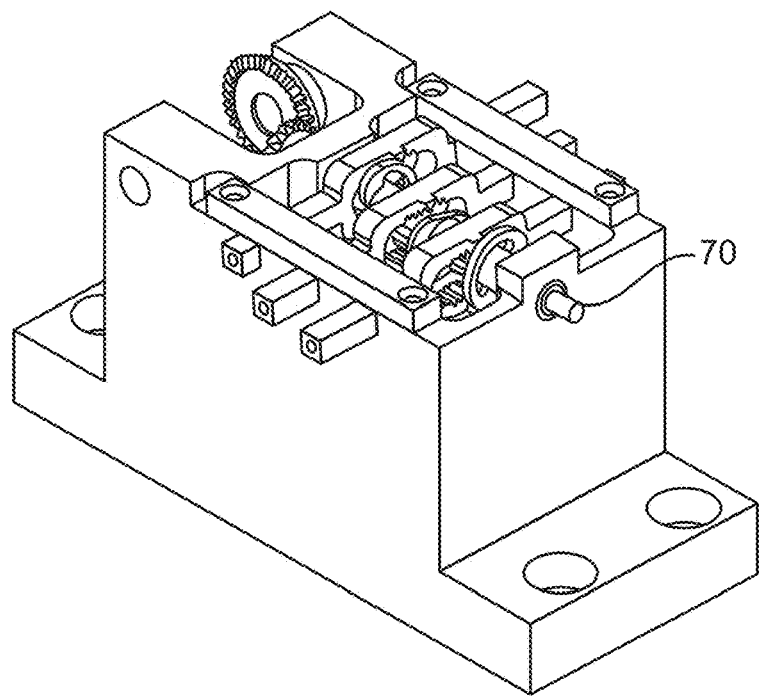
FIGS. 23A and 23B are a perspective view and a top plan view of a conversion assembly implementing rack and pinion assemblies of the type shown in FIG. 22A.
Figure 23B:
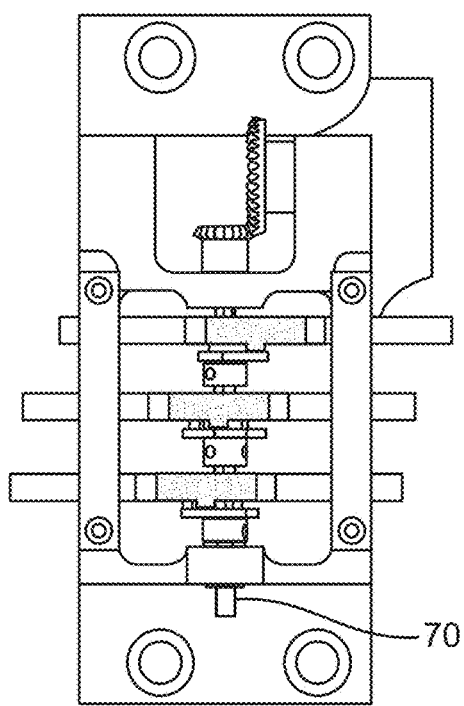
Figure 24A:
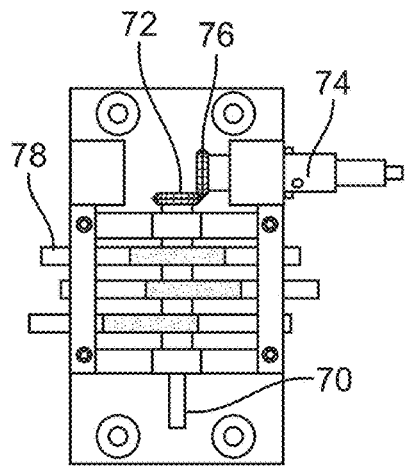
FIGS. 24A-24F is a sequence of images illustrating the action of the pistons of the assembly of FIG. 23A in response to rotation of an associated shaft.
Figure 24B:
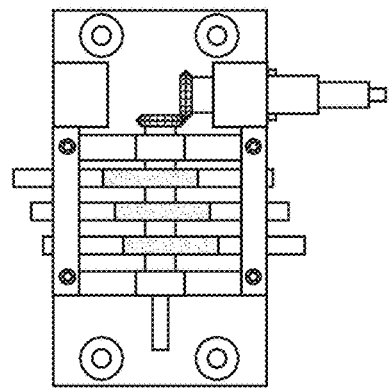
Figure 24C:
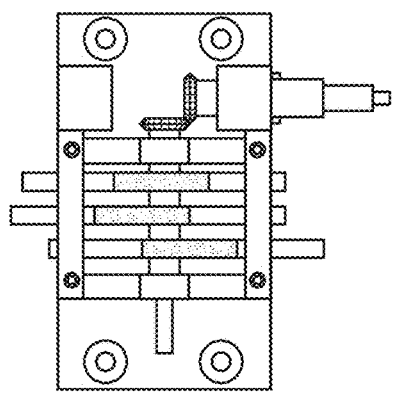
Figure 24D:
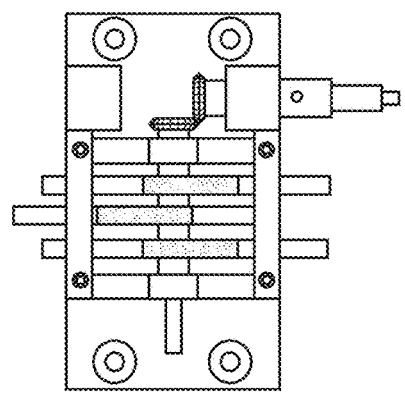
Figure 24E:
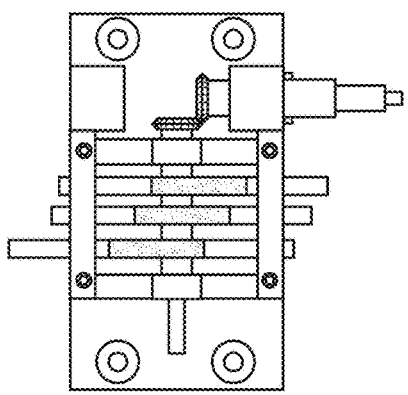
Figure 24F:
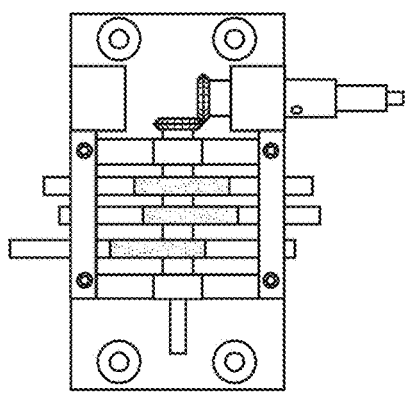

FIGS. 23A and 23B illustrates rack and pinion assemblies of the type described above arranged in a manner that will convert linear motion to rotary motion, and that will convert rotary motion to linear motion. Three rack/pinion assembles are arranged with their pinions mounted on a common shaft 70. Each pinion is at a different phase of its rotation, so that its corresponding rack is at a different point along its travel as best shown in FIG. 23A. In this specific configuration, each pinion is 120 degrees out of phase with the pinion of the adjacent rack(s).

For converting rotary motion to linear motion, the shaft 70 is driven, with the rotation of the shaft 70 (and the pinions mounted to it) resulting in translation of the racks. The motor shaft used to drive the shaft 70 may be directly connected to or integral with the shaft 70, or its motion may be coupled to the shaft by gears. In this embodiment, shaft 70 has a first gear 72. The motor drives a second shaft 74 (not shown in FIGS. 23A and 23B, but see FIG. 24) that has a second gear 76 connected to it.

For converting linear motion to rotary motion, application of linear force to the pistons at one end of each of the pinions results in rotation of the shaft 70. That rotary motion can be transferred to another shaft such as shaft 74.

FIGS. 24(a)-(f) are a sequence of photos of a prototype system showing a sequence of motion of the pistons 78 of the three racks as the shaft 74 is manually rotated.

The disclosed rack and pinion assemblies may be incorporated into both the drive side to convert rotary motion into linear motion for transfer across a sterile barrier such as a drape, and/or incorporated into the surgical device to convert linear motion received from across the sterile barrier into rotary motion that can be used to roll a part of the surgical device.

To incorporate the rack and pinion assemblies into the surgical system described above, a first assembly of the rack and pinion assemblies may be disposed in the surgical device housing (like housing 4 FIG. 8), with the pistons 78 of the racks replacing (and serving as) the input elements 28*d* of the surgical device and with shaft 74 being the device shaft 16 or an inner shaft that extends through the device shaft 16 and supports the end effector.

A second assembly of the and pinion assemblies may be disposed in the motor drive, with a motor positioned to drive the shaft 70 either directly or via an intervening gear assembly as discussed above.

Note that while incorporation of the rack and pinion assemblies into both the drive (motor drive) side and the driven (surgical device) side of the system is described, this is not a requirement. One embodiment might use the rack and pinion assemblies on the surgical device side, and an alternate assembly for translating the output elements on the drive system. As an example, each output element could be controlled by a separate motor.

Another embodiment might use the rack and pinion assemblies on the motor drive side, and an alternate assembly on the surgical device side for receiving the linear motion and converting that linear motion to rotary motion used to effect instrument roll.

Note also that the drawings of the third embodiment show bench prototypes and so the packaging configurations may differ once the assemblies are incorporated into the motor drive assembly and surgical device of the surgical system.

Figure 25A:
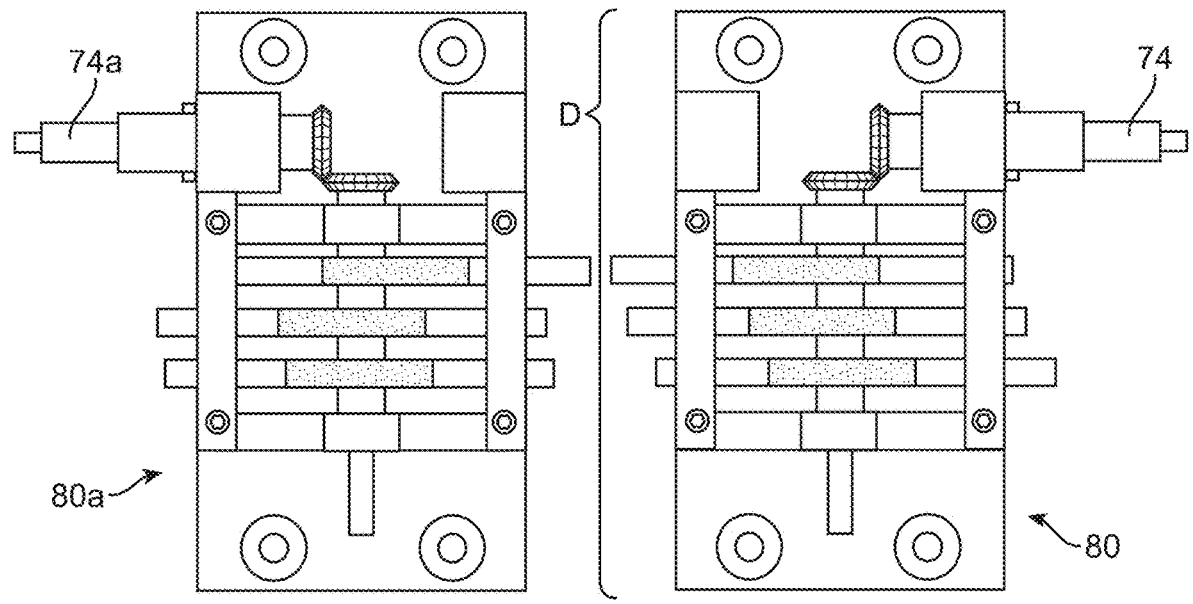
FIGS. 25A and 25B illustrate an arrangement of two FIG. 23A assemblies.
Figure 25B:
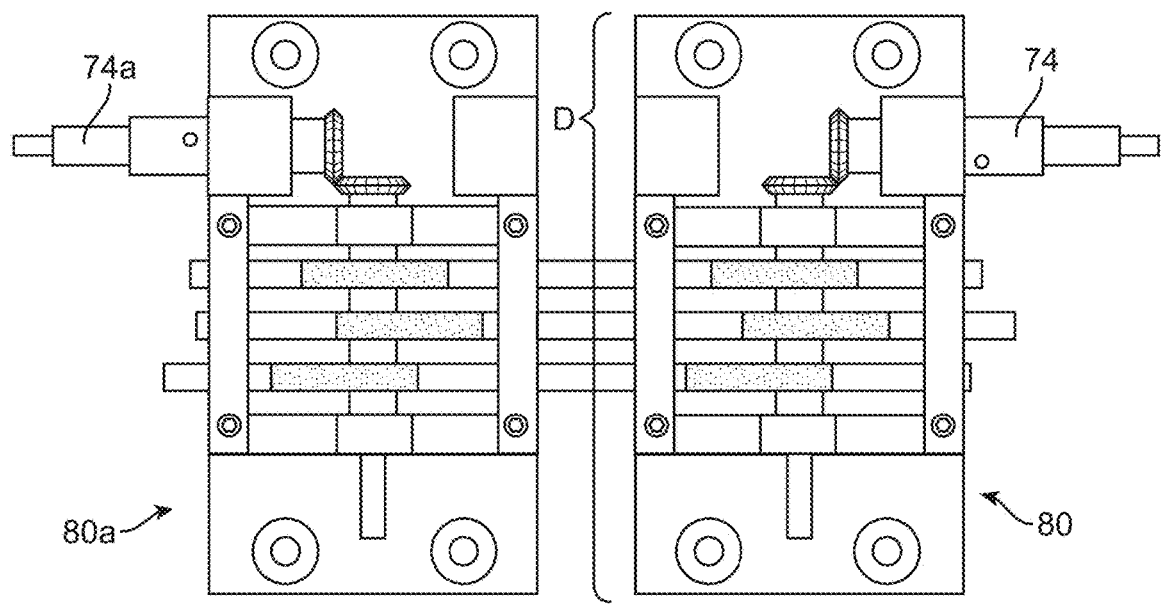
Figure 26A:
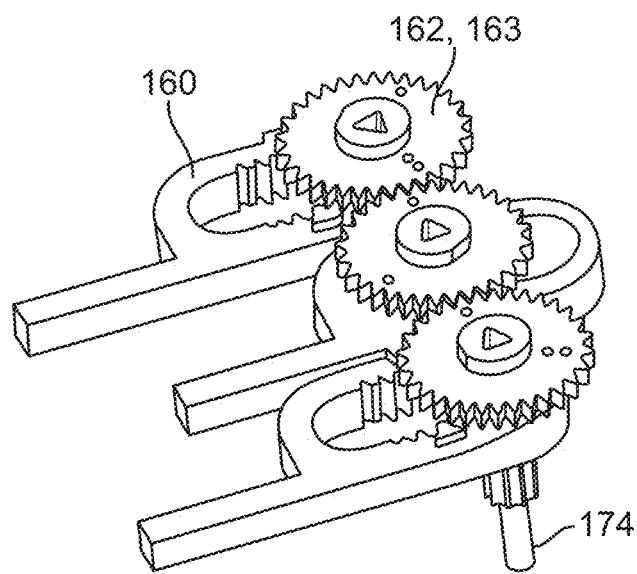
FIGS. 26A and 26B are perspective views showing an assembly of racks and pinions that is an alternative to that shown in FIG. 23A.
Figure 26B:
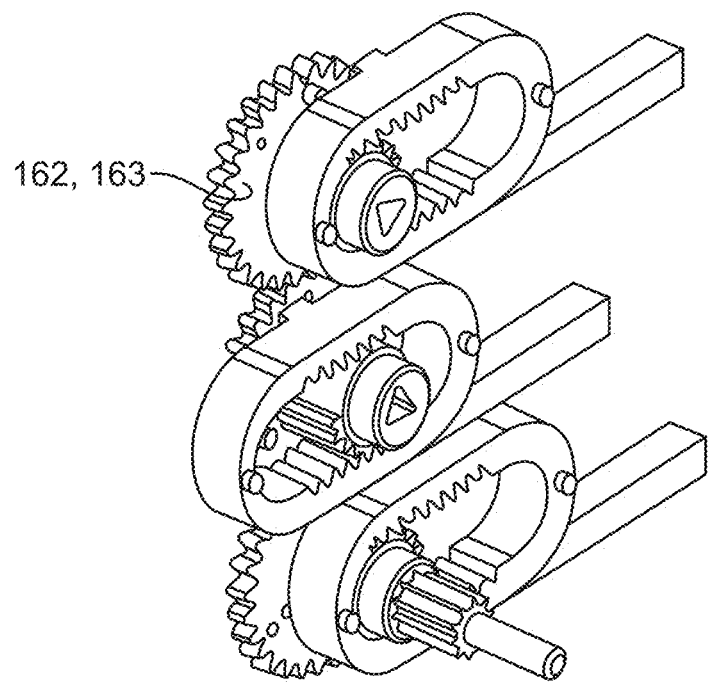

Referring to the prototype systems shown in FIGS. 25 and 26, assume that the system 80 on the right is incorporated into the motor drive with a motor driving the shaft 74, and the system 80*a* on the left is incorporated into the surgical device, with the surgical device shaft (either outer or inner shaft as discussed above) is the shaft 74*a*. Surgical drape D covering the motor drive assembly is positioned between the pistons of the systems 80, 80*a*, and the pistons of the assembly 80*a* (which are the surgical device's input members for the roll function) are brought into alignment with the pistons of the assembly 80 (which are the motor drive's output/drive members for the roll function), with the drape D sandwiched between them as shown in FIG. 26. Note that while the pistons at the opposite ends of the racks (relative to the drape) are visible in the drawings, when the systems are incorporated into the motor drive assembly and the surgical device, these extra pistons need not be exposed.

When the motor associated with shaft 74 is rotated in a first direction, the reciprocating, out of phase, motion of the three pistons of the assembly 80 produces corresponding reciprocated, out of phase, motion of the three pistons of the assembly 80*a*, causing continuous rolling of the shaft 74*a*. When the motor is reversed to rotate the shaft 74 in the opposite rotation, the direction of rotation of the shaft 74*a* is likewise reversed.

Figure 29:
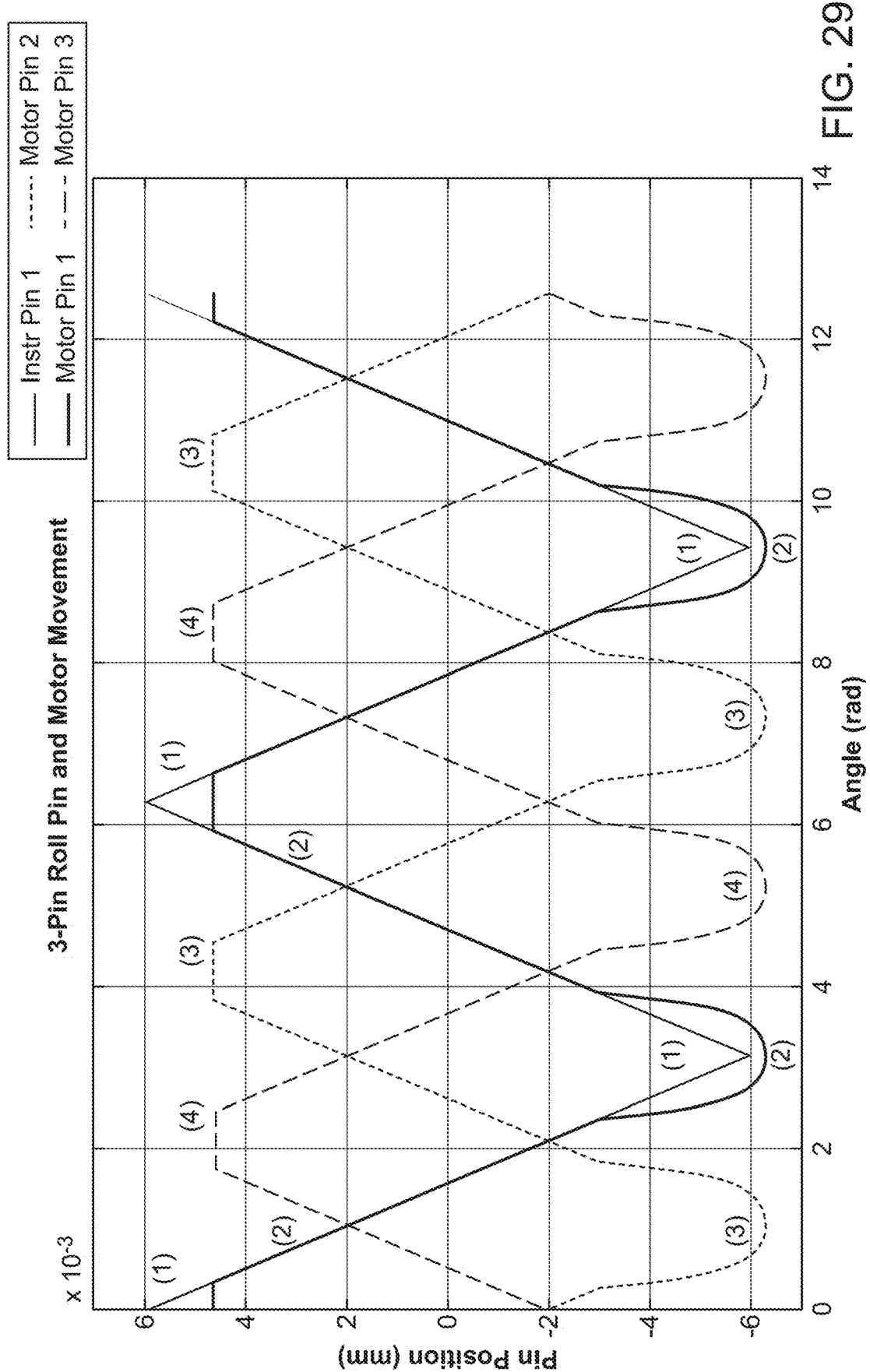
FIG. 29 graphically depicts movement of the three output drive elements of the third embodiment over time.

In one implementation of the third embodiment, the motor drive is arranged to use three motors to linearly drive three output drive elements. In this implementation, the motors are configured so as to drive one output drive element (pin/piston) at a time. FIG. 29 graphically depicts movement of the three output drive elements over time, and shows how they move out of phase from one another. The blue line (1) is the path that instrument pin #1 takes. The orange, yellow and purple lines (2), (3) and (4) are paths of motor-driven pins 1, 2, and 3 respectively. The paths are plotted versus the desired roll angle in radians (x-axis). Each motor pin uses the same function, but has a phase offset of 0, 120 and 240 degrees.

Figure 30:
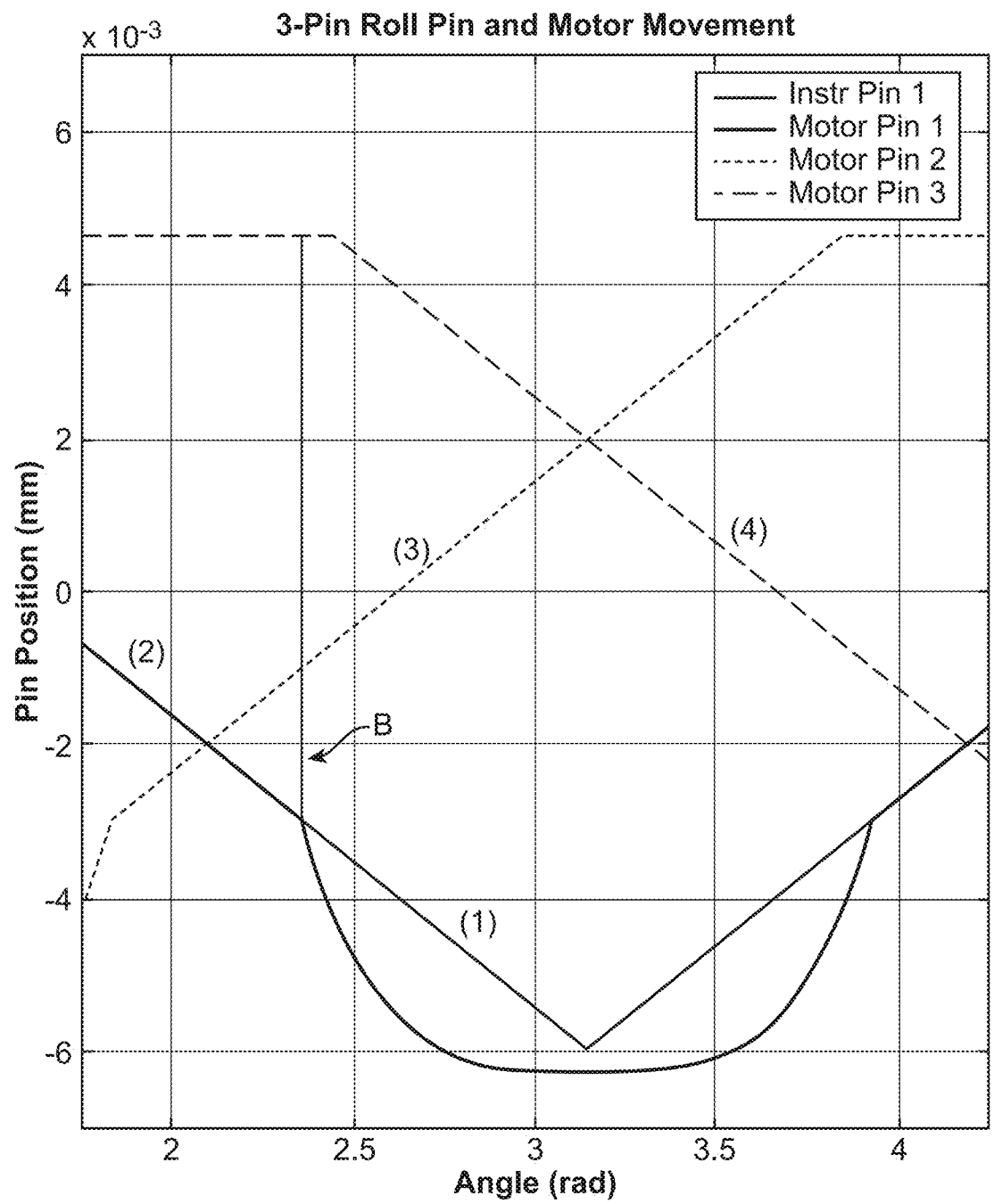
FIG. 30 is an enlarged view of a portion of FIG. 29.

The algorithm used to control the motors helps the system to avoid binding of the rack and pinion assemblies. It can be seen at the top of the wave that the motor pin is caused to stop moving at a distance of 1.3265 mm before the tip of the instrument pin, so as to allow the other components of the instrument roll mechanism to move the pin through its "turn around" zone. Additionally, the algorithm is constructed to insure that the instrument pin does not bind at the bottom of the wave. For this purpose, a 4th order polynomial (quartic) wave is added to the bottom to smoothly move the motor pin out of the way (its bottom position is 0.25 mm below the bottom of the instrument pin triangle wave.) In order to ensure that two pins are not simultaneously pushed (an action that can cause binding), the "disengagement" point where transition is made from the linear section to the polynomial curve is designed to overlap with the other pin's "flat" area by a few degrees to ensure that motor pin 3 is still stationary in its "flat" zone when motor pin 1 is moved away from the instrument pin. See the enlarged section of the chart shown in FIG. 30, where a black line marks the point at which motor pin 1 is disengaged from the instrument pin. This small amount of "dead zone" where no motor is driving a pin forward ensures that only one pin actively drives the mechanism at once. The quartic function was designed to smoothly move the pin back to its minimum position more quickly than could be achieved using a 2nd order polynomial (quadratic) curve.

It should be pointed out that while FIGS. 23A-25B show the pinions for the racks mounted to a common shaft (where each pinion is out of phase with the others to enable continuous rotation of the pinion shaft), in an alternative embodiment the pinions for each rack need not share a common shaft.

FIG. 26 shows an embodiment in which each pinion 162 has its own axis (three pinions are shown. Each pinion 162 includes a spur gear 163 that moves integrally with the pinion. The pinions interface with one another via these spur gears. The manner in which the pinions 162 move within the racks 160 is similar to that described above.

Where the assembly is used on the driven side (as part of the surgical device assembly 12), one of the pinions has a belt pulley our other output assembly coupled to its rotary motion such that the belt translates the rotation of the mechanism to the output shaft 174 for end effector rotation. Where the assembly is used on the drive side (as part of the motor drive assembly), shaft 174 is an input shaft that receives rotational motion from a motor, causing linear motion of the pistons extending from the pinions, whose reciprocating pistons may thus transmit the linear motion through the drape in the manner described above.

It should also be noted that although the embodiments shown above use three or more pins for effecting rotation (a configuration particularly useful when only pushing is being carried out between the drive pins and the driven pins, as opposed to both pushing and pulling. While those embodiments can be used in systems that make use of both pushing and pulling between the drive side pins and the driven side pins, push/pull systems can also make use of as few as two pins, which may be out of phase with one another by 90 degrees.

Figure 27:
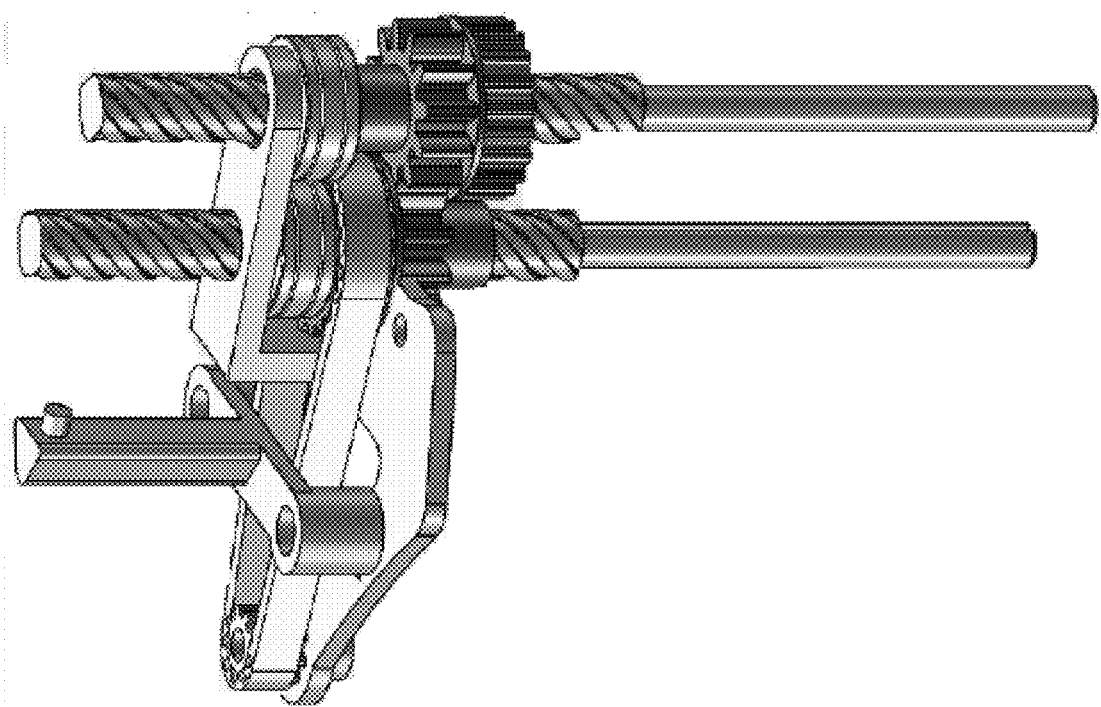

A fourth embodiment of an assembly for converting linear motion to rotary motion is shown in FIG. 27. This configuration may be incorporated into the surgical device so that linear motion transferred from output elements of the motor drive (across the drape) is received and converted to rotary motion for rolling the surgical device shaft. The fourth embodiment uses two parallel lead screws, spaced apart such that the gear molded or cut into the lead screw nuts sync. The lead screws must be keyed so that they do not rotate. When the lead screw is translated, it forces a rotation on its corresponding nut. The gear on that rotating nut forces rotation of the adjacent nut in the opposite direction. The rotation of the adjacent nut forces translation of the adjacent lead screw. Therefore, pushing one lead screw forward results in a reverse translation of the adjacent lead screw.

In this embodiment, the lead screw nut also has a timing belt pulley molded or machined into its outer diameter. Rotation of that nut drives a belt and another pulley to perform a desired action—in this case that action is instrument rotation. This system requires a balancing of torque and amount of rotation—which can be optimized based on the lead screw selection and gear train ratio on the belt drive.

Figure 28:
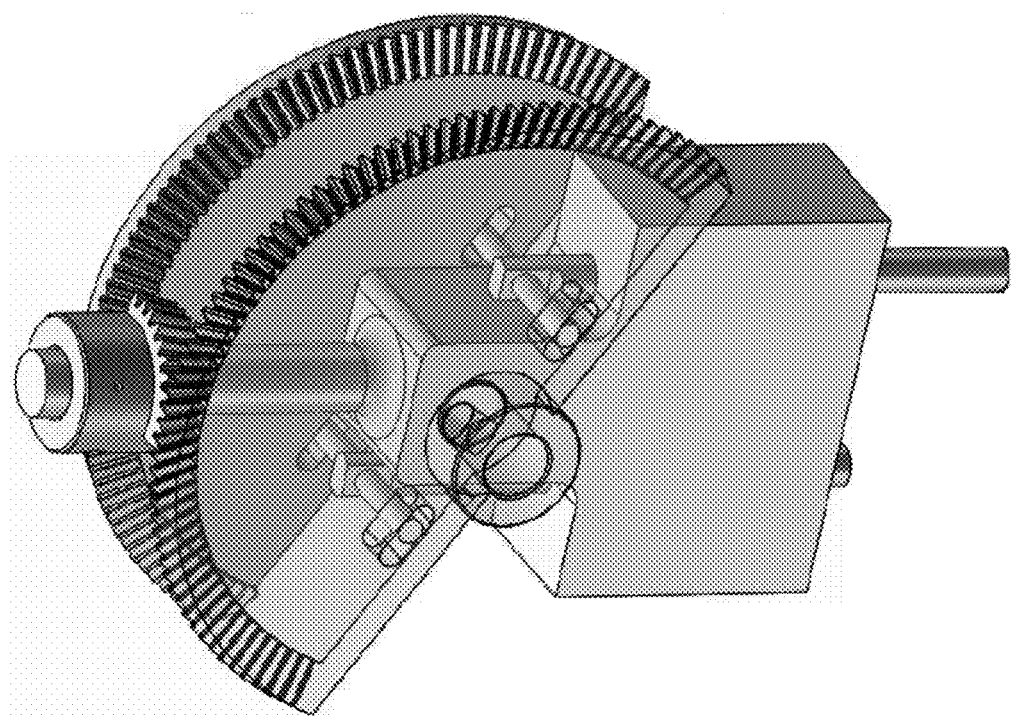
FIGS. 27 and 28 show alternate embodiments of conversion assemblies.

A fifth embodiment of an assembly for converting linear motion to rotary motion is shown in FIG. 28. This embodiment consists of two pistons, each engaging with two half-circle bevel gear "racks". Translating one piston forward tilts both bevel gears in one direction and translates the adjacent piston in an equal and opposite direction.

The bevel gear racks are positioned to interface with a centrally located partial bevel gear. Gear tooth timing is crucial to this concept. The partial bevel gear only interfaces with one side of the rack at a time. When that rack is tilted in one direction or the other, the bevel gear is rotated in a direction corresponding with the rack tilt.

At the end of travel for the rack, the partial bevel gear is designed to jump to the adjacent track, such that tilting the racks back in the other direction actually results in the same direction of rotation on the bevel gear. This enables continuous rotation of the bevel gear where the partial bevel gear jumps from rack to rack at the end of piston stroke.

A sixth embodiment is similar to the FIG. 16 embodiment. It can be operated with 3 or more pistons, equidistant (or not) and having parallel axes (or not). Each piston interfaces with an intermediate part that helps compensate for changes in angles in 2 directions. The part can be shaped like a "T", such that the primary leg of the "T" is rotationally connected to each piston. This allows the "T" part to rotate in an axis that is perpendicular to the axis of the piston. The top part of the "T" is rotationally connected to a wobble plate such that it can provide an additional degree of rotation during movement.

The wobble plate toggles back and forth about a centrally located pivot. As it toggles back and forth, it interfaces with a centrally located shaft that has two diameters. The first diameter is the primary rotation axis and the shelf between the first and second diameters is angled relative to the shaft axis. The wobble plate interacts with the angled shelf such that pushing the wobble plate forces rotation on the centrally located shaft. The rotation can be reversed by reversing the direction of the piston movement.

This concept is used in axial engine design. In embodiments where the drive elements are configured to both push and pull the input elements (as opposed to only pushing them), this embodiment could be modified to reduce the number of pistons to 2 pistons operating out of phase with one another (most efficient at 90 degrees out of phase).

A seventh embodiment is a slider crank embodiment which makes use of two or more pistons, with the pistons operating out of phase with one another. The pistons interface with a rotary component through an intermediary linkage. The pistons may be oriented such that they have equal and opposite translation, or they could operate out of phase such that their translation is not equal and opposite.

Each piston has a linkage connected at the top of the piston and the other end of each linkage is connected to a wheel (or crank). Translating a piston forward causes rotation of the wheel. Rotation of the wheel forces the adjacent piston to move as well.

This concept can be operated with more than two pistons and, if the drive/output elements are configured to both push and pull the input elements, two pistons can be used to create continuous and reversible rotation on the wheel, assuming the two pistons operate out of phase with one another. This allows second piston to still generate rotation when the first piston is at its indeterminent locations The motor drives and surgical devices described herein are components of a surgical system that includes a user input device used by a surgeon to input instructions to the surgeon as to the desired movement or actuation of the surgical devices. The surgical system further includes a control system including one or more processors that receive signals from the user input devices and from sensors of the system, and that generate commands used to drive the motors to cause active bending, deployment, actuation, etc. of the surgical devices in accordance with the user's input. A display for displaying an image obtained from a scope within the body cavity (e.g. a scope positioned and manipulated as described herein) is typically positioned in proximity to the user input device, allowing the surgeon to view the image of the procedure while s/he operates the user input device. User input devices and control systems for robotic surgical systems, and laparoscopic/endoscopic image displays are known to those skilled in the art and so details of such systems are not provided herein.

To use the system, the hospital staff positions sterile drapes over the motor drive units, with the sterile drape material extending over the output elements. This step may be performed with the motor drives mounted to the support. Surgical devices are mounted to the system to position the input elements in a drive relationship with their corresponding output shafts, with the sterile drape disposed between the input elements and output elements. During use of the system, the surgeon operates the input devices while observing the procedure on the display. The control system operates the motors in response to user input so as to articulate, deploy, roll and actuate the surgical instruments in accordance with the user instructions.

In any of the disclosed embodiments, the motors used for driving may be replaced with other types of drivers including, without limitation, hydraulic or pneumatic drivers. Mechanical communication is possible by means of hydraulic actuation transmitted across the drape, without penetrating the drape.

Open Robotic Manipulator Platform and Attachable Implements

Figure 31A:
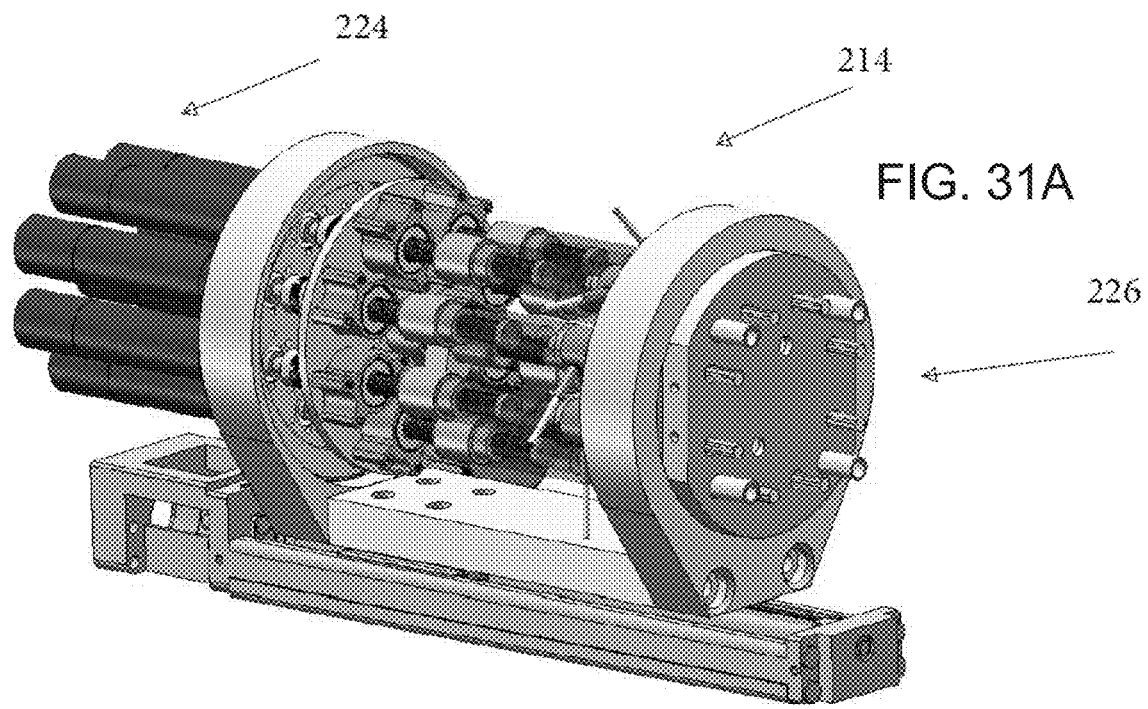
FIGS. 31A through 31C are perspective views of various configurations of drive assemblies.
Figure 31B:
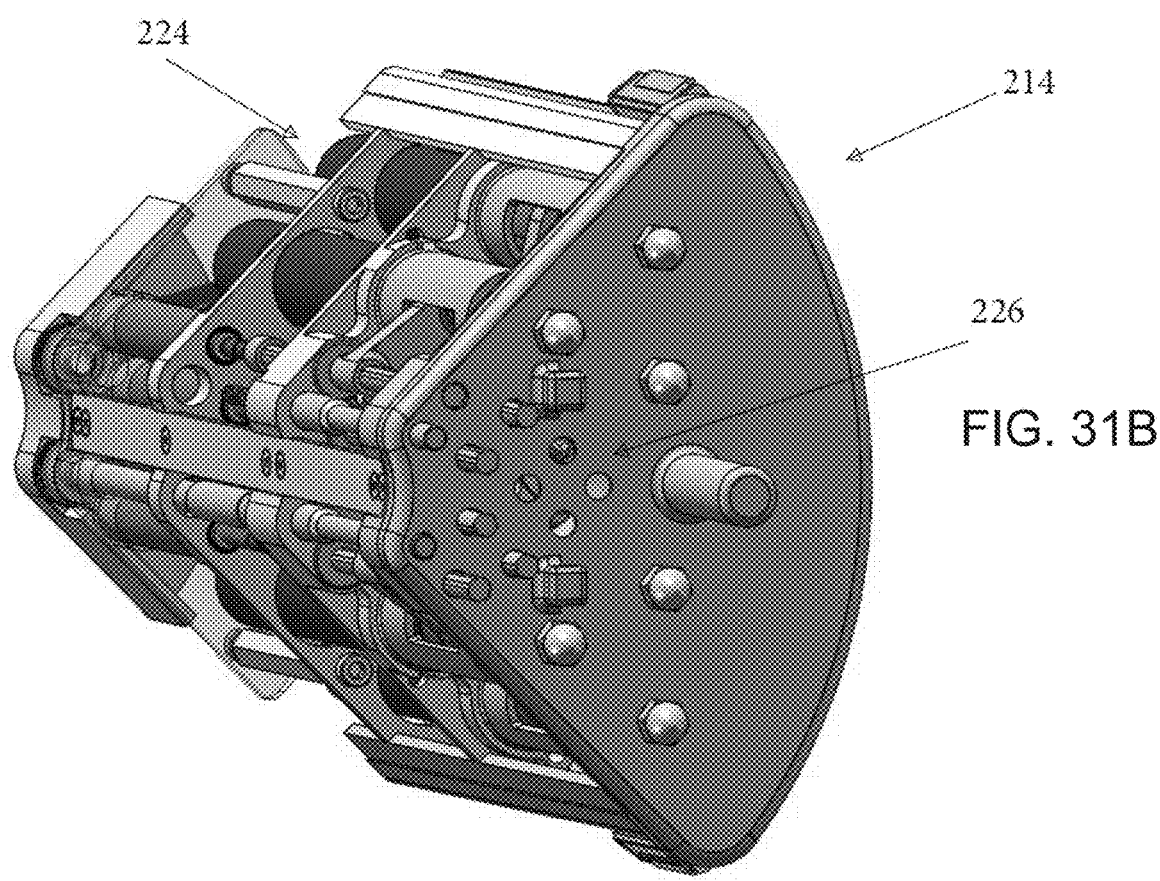
Figure 31C:
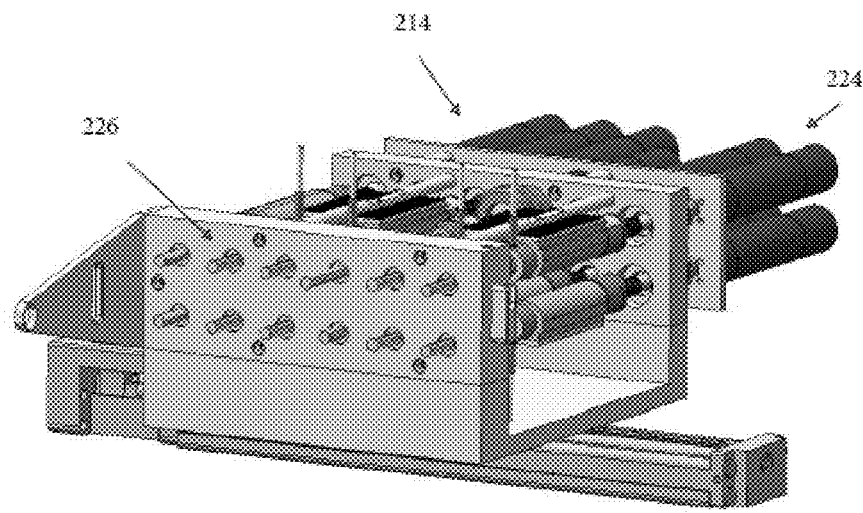

In a system of the type described in the '098, a robotic system includes a drive assembly/motor assembly 214 (which may be like motor drive assembly 14 described above) providing exposed output elements 226 such as the pins/pistons described above having linear displacement that can be precisely controlled. The motors 224 and the corresponding pins 226 can be arranged in a variety of patterns/arrays to create an overall configuration of pins/pistons, including the configurations described in the '098 as well as those shown in FIGS. 31A-31C.

A surgical robotic system of this type may provide an open platform that can be used for various types of instruments having functions (instrument roll, articulation in one or more degrees of freedom, jaw actuation, etc.) that are actuated using linear input, without requiring that particular drive pins 226 be used to actuate a particular type of function. In other words, a particular drive pin might actuate one function (e.g. shaft articulation or bending) when one surgical device is mounted to the motor drive assembly, yet actuate a different function (e.g. instrument roll) when a different surgical device is mounted to that motor drive assembly. This allows creation of an array or pattern of any number of motors against which instruments can be assembled over a sterile drape.

The motor array and corresponding pin arrangement may have any number of different arrangements. For the purposes of this description, the drive pins 226 are arranged in a 2×6 arrangement as shown in FIGS. 32A-32E. This may achieved by arranging the motors 224 in the rectangular configuration shown in FIG. 31C. As will be understood from the description of FIGS. 32A-32E that follows, the drive system allows a single drive array to used with a variety of interchangeable instruments without requiring that particular pins of the drive array be dedicated to just a single surgical device function.

Figure 32A:
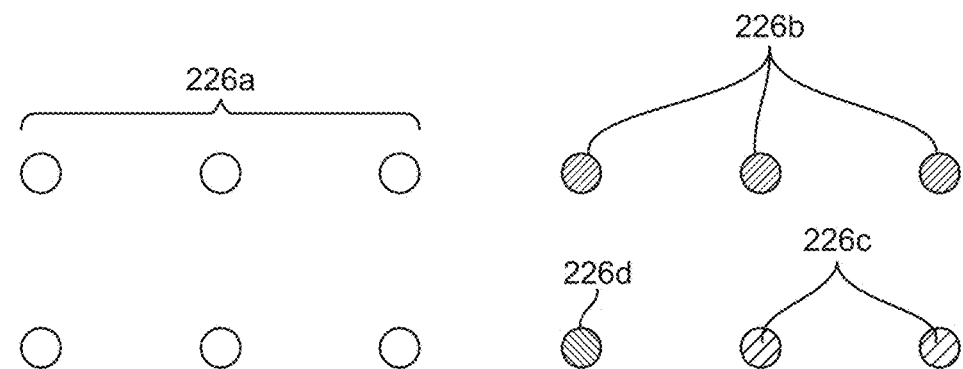
FIGS. 32A through 32E schematically illustrate arrays of drive pins for a drive assembly.

Referring to FIG. 32A, the illustrated circles represent drive pins/pistons 226a, 226b, 226c, 226d. In exemplary systems, each such drive pins may be capable of moving from 0 mm to 20 mm with the same precision and load. A variety of instruments can be designed around these inputs to enable any number of feature sets.

For example, the pattern of FIG. 32A, below, read from left to right, describes an instrument that has six pins dedicated to articulation (pins 226a), three pins dedicated to instrument roll (pins 226b), and two pins (226c) dedicated to jaw actuation (green). The remaining pin 226d is un-utilized for this particular instrument.

Figure 32B:
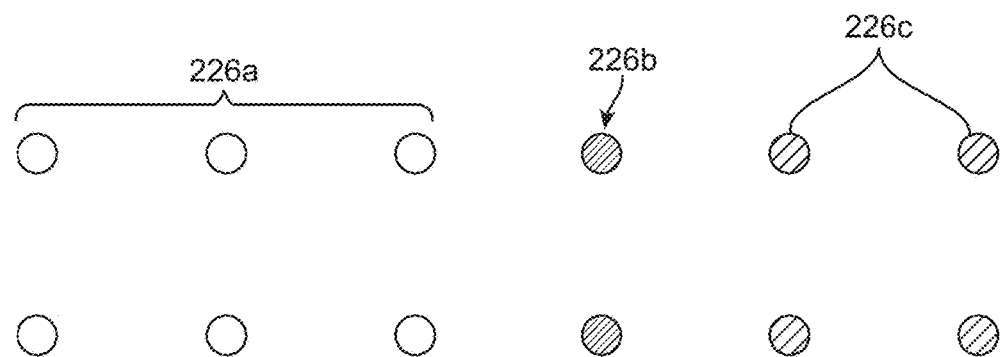

In another example shown in FIG. 32B, the first 6 pins 226a are dedicated to articulation, the next column of pins 226b are used for instrument roll, and the two columns of pins 226c on the right may be used to articulate the surgical instrument's end effector or actuate a wrist mechanism.

Figure 32C:
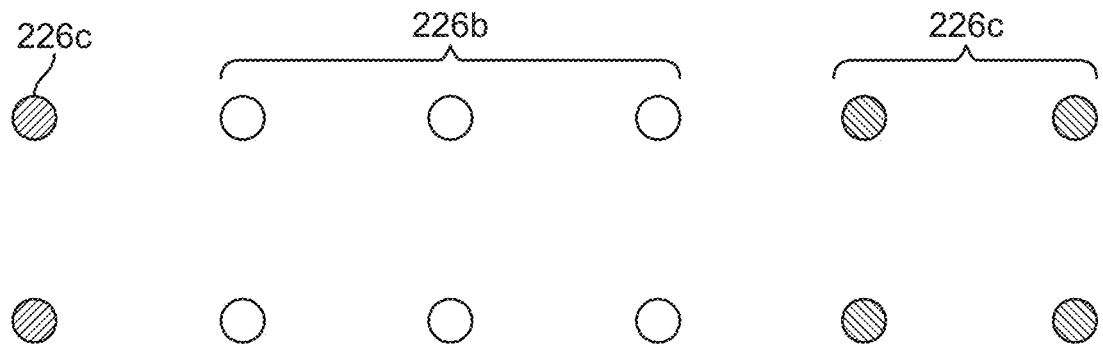

In a third example shown in FIG. 32C, the first column's two pins 226a might enable instrument roll, while the next six pins 226b allow for articulation, and the final pins 226c are not utilized for that particular instrument.

Figure 32D:
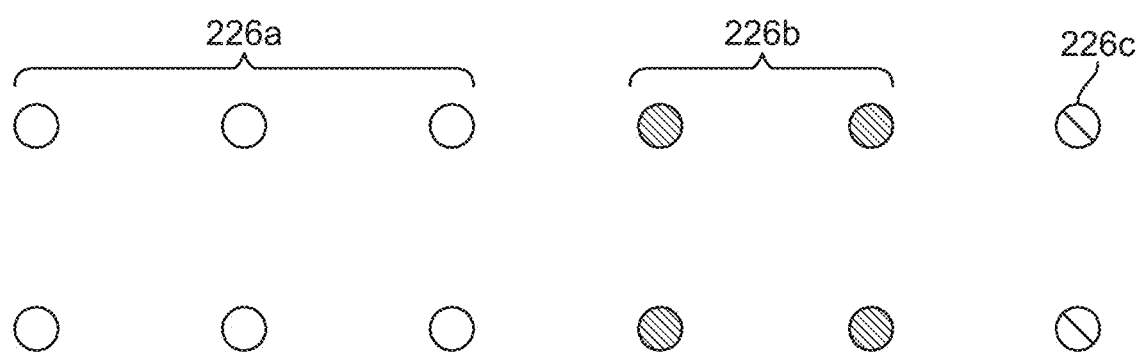
Figure 32E:
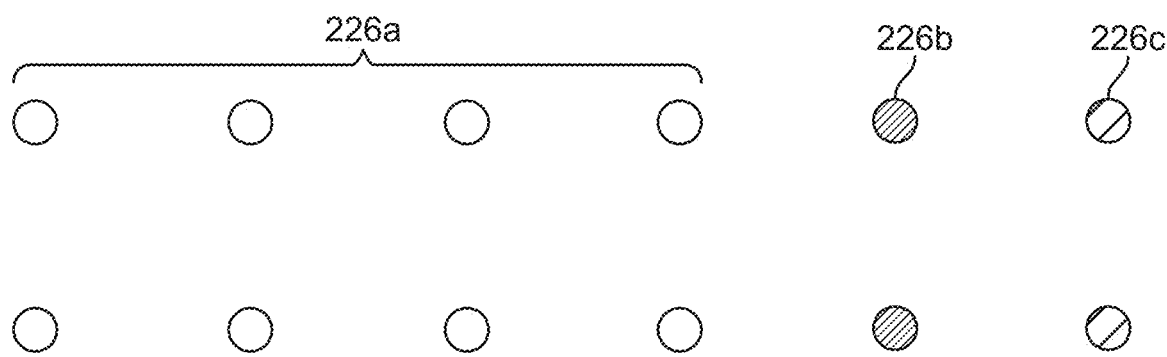

Still another example could be a suction/irrigation application where more than one surgical device may be positioned at a single motor array. Referring to FIG. 32D, as one example of such an arrangement, the six pins 226a of the first three columns may enable articulation as before, the pins 226b of the next two columns are un-used, the last two pins 226c (the far right column) are used to operate a valve mechanism to switch between three positions: (1) Off, (2) Suction Enabled and (3) Irrigation flow. In this case the valve mechanism may be removeably attached to the articulation device, the articulation device having a channel through which fluid may pass in either direction.

All of the above examples use six pins for actuating articulation of the surgical device. However, any number of pins could drive any number of mechanisms to provide motion of the end effector. For example, the FIG. 32E arrangement could be used for an instrument that has eight actuators (corresponding to pins 226a) for tip positioning, two actuators (corresponding to pins 226b) for performing roll and two actuators (corresponding to pins 226c) for performing jaw actuation.

The above examples provide only a small subset of what is possible with this particular motor array. Other shapes of arrays are possible, including a 3 row×4 column array, a cylindrical array as described above or even a non-uniform array if such a motor array were required for space or design reasons. A motor drive using twelve actuation pins could be used to actuate the functions needed for both simple and complex surgical devices, including surgical staplers and advanced energy devices.

With this type of drive system, an electromechanical surgical system can be provided that includes a uniform motor array, in which each driver is configured to have the same range of travel, precision, speed and force. This enables instruments to be designed with any degree of freedom cascade desired The following description relates to a configuration in which the surgical device 212 is a robotically-controlled, steerable open lumen instrument, which may have functions (e.g. bending/articulation) that can be driven as described in the '098 using a first subset of the available pins of the drive assembly, and to which other auxiliary devices 213 can dock and have their functions actuated by the drive assembly 214 of the robotic system via a second subset of the pins of the drive assembly. Thus both the surgical device 2121 and auxiliary device can be driven or actuated via the robotic user interface, by way of the pin actuators on a common drive assembly.

Figure 33A:
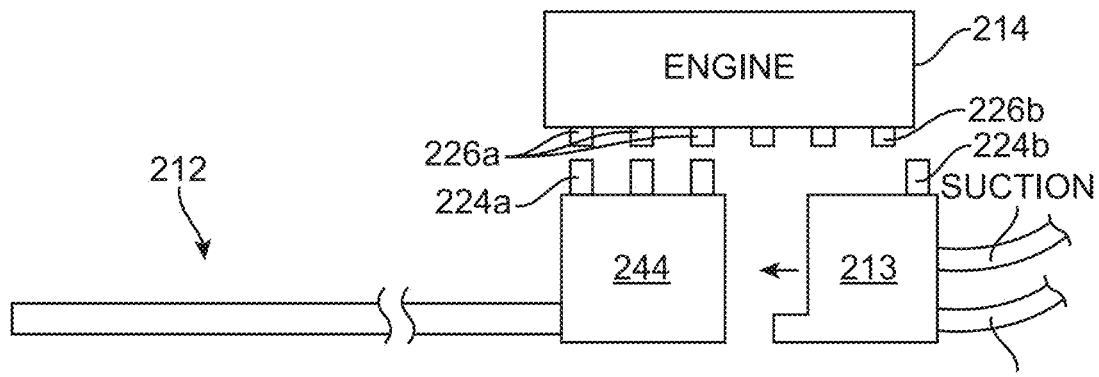
FIG. 33A illustrates an assembly of a drive assembly, surgical device, and auxiliary device.
Figure 33B:
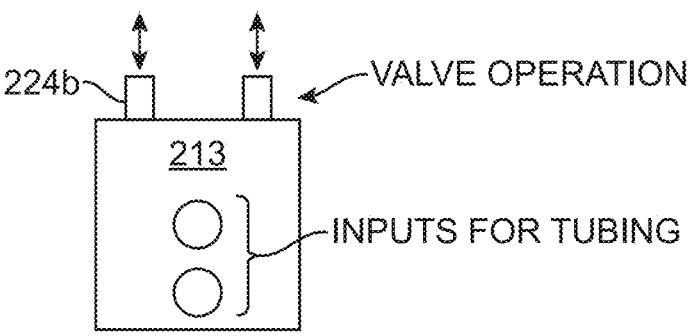
FIG. 33B is a rear elevation view of the auxiliary device shown in FIG. 33A.

An embodiment shown in FIGS. 33A and 33B includes a surgical device 212 that includes an instrument housing and shaft with a steerable distal end. Input pins 224a of the surgical device receive linear motion from output pins 226a of the drive assembly 214 to control this steering function, as described in the '098 application. The instrument shaft is an open lumen that can be used to pass fluids or catheters, surgical tools or materials, directed to and from a desired location in the surgical site. The instrument housing 244 and/or drive assembly frame enables docking of the auxiliary devices 213 so they can be supported during use.

Drive pins 226b on the drive assembly 214 deliver motion to drive pins 224b on the auxiliary instrument in order to actuate its functions. For example, the auxiliary instrument 213 docked to the steerable open lumen instrument may be a suction irrigation implement fluidly coupled to the open lumen so that the suction irrigator can administer fluid through the open lumen of the open lumen, or be used to evacuate fluid from the surgical site through the open lumen. Drive pins 226b of the drive assembly drive pins 224b of the suction irrigation implement, which are operatively associated with the function of the valve system within the suction irrigation implement 213. Thus, movement of pins 224b actuates the valve system to selectively deliver/terminate administration of irrigation fluid and/or suction based on input given to the robotic system by the surgeon or the surgical staff (e.g. using a surgeon input devices at the surgeon console).

Figure 34:
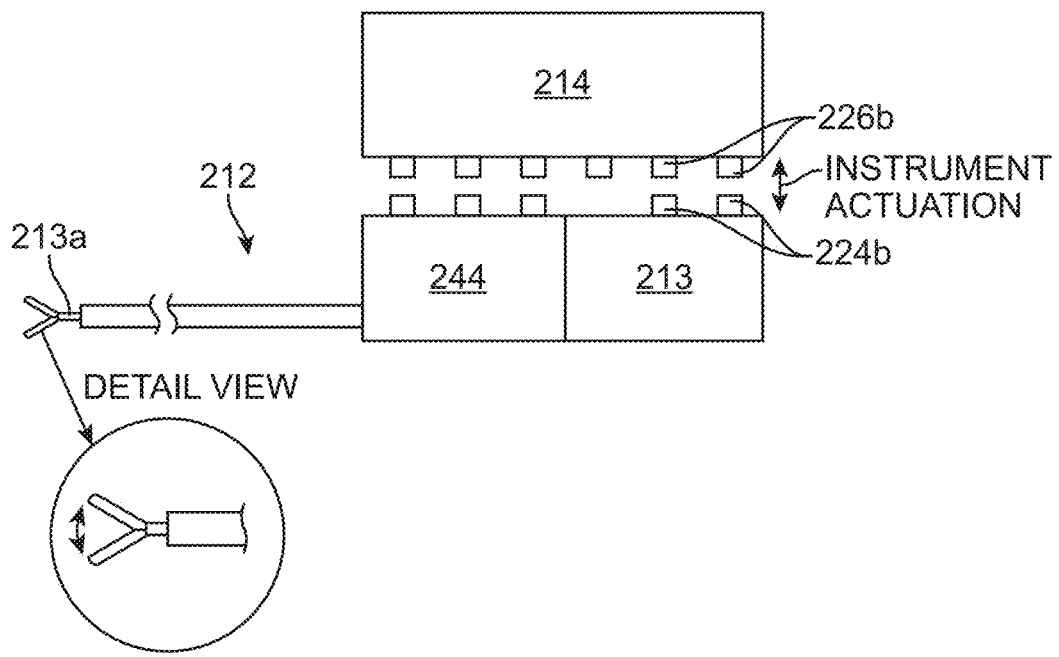
FIG. 34 illustrates a second embodiment of an assembly of a drive assembly, surgical device, and auxiliary device.

Referring to FIG. 34, another example of an auxiliary device 213 is a biopsy tool that is passed down the shaft of the open lumen instrument. Movement of the biopsy jaws 213a is actuated by delivering motion from the drive pins 226b to the inputs 224b as previously described, while steering of the shaft of instrument 212 is actuated by a different subset of the drive pins as discussed above.

In a modification of the FIGS. 33A and 34 embodiments, the auxiliary device may be a diagnostic device, such as a multispectral fiber-optic tool that can be being passed down the open lumen of the instrument and steered into place (through motion of the steerable surgical device) where the fiber-optic tool can be used to perform a tissue analysis.

The open platform robotic surgical system described here can be used to allow disposable surgical instruments to attach to a re-usable or limited-life steerable instrument in a way that the disposable instrument can be steered about the abdomen and actuated to perform specific surgical tasks.

While certain embodiments have been described above, it should be understood that these embodiments are presented by way of example, and not limitation. It will be apparent to persons skilled in the relevant art that various changes in form and detail may be made therein without departing from the spirit and scope of the invention. This is especially true in light of technology and terms within the relevant art(s) that may be later developed. Moreover, features of the various disclosed embodiments may be combined in various ways to produce various additional embodiments.

Any and all patents, patent applications and printed publications referred to above, including for purposes of priority, are incorporated herein by reference.

We claim:

1. A surgical system comprising:
   a drive unit on a support, the drive unit comprising a plurality of actuators and a plurality of output elements, each actuator operable to linearly translate a corresponding one of the output elements;
   a surgical device comprising
      an elongate device shaft,
      an input subsystem carried at a proximal end of the shaft, the input subsystem including a plurality of input elements each operatively associated with a linear-to-rotary conversion assembly, each input element linearly translatable;
   wherein the surgical device is removably mounted relative to support to position each output element in a drive relationship with a corresponding input element; and
   wherein operation of an actuator linearly translates an output element, causing linear translation of a corresponding input element and axial rotation of the elongate device shaft.

2. The surgical system of claim 1, wherein each output element and its corresponding input element is linearly translatable along a common axis.

3. The surgical system of claim 1, wherein each input element is mechanically engaged to its corresponding output element.

4. The surgical system of claim 1, wherein each input element magnetically interfaces with its corresponding output element.

5. The surgical system of claim 1, wherein the elongate device shaft is an outer shaft or an inner shaft extending through an outer shaft.

6. The surgical system of claim 1, wherein each input element is not mechanically attached to its corresponding output element.

7. The surgical system of claim 1, further including a sterile drape positionable between the input elements and the output elements.

8. The surgical system of claim 7, wherein the input and output elements do not penetrate the drape.

9. The surgical system of claim 1, wherein the conversion assembly includes a shaft having a cam surface, each of the input elements coupled to the shaft such that translation of each input element against the cam surface causes rotation of the shaft, the shaft and the device shaft arranged such that rotation of the shaft results in rotation of the device shaft.

10. The surgical system of claim 9, wherein the cam surface is defined by a collar on the shaft.

11. The surgical system of claim 9, wherein the cam surface is defined by a groove in the shaft.

12. The surgical system of claim 9, wherein the shaft has a first end, and wherein the cam surface is a continuous curved surface encircling the shaft and having at least two apex sections, including a first apex section and a second apex section, the first apex section closer to the first end than a second apex end.

13. The surgical system of claim 12, wherein the first and second apex sections are separated 180 degrees around the shaft.

14. The surgical system of claim 1, wherein the conversion assembly includes a shaft and plurality of rack and pinion assemblies, each rack and pinion assembly including a pinion mounted to the shaft, and
a rack that is engaged with the pinion such that linear translation of the rack produces rotation of the pinion and that includes one of the input elements,
wherein each rack is positioned relative to its corresponding pinion such that the racks move linearly relative to the shaft, the linear motion of each rack being out of phase with that of the other racks such that a collective motion of the racks causes continuous rotation of the shaft, and wherein the shaft and the device shaft arranged such that rotation of the shaft results in rotation of the device shaft.

15. The surgical system of claim 13, wherein each rack and pinion assembly further includes a cam surface disposed on the rack and a follower carried by the pinion, the cam surface and follower shaped such that when teeth of the rack and pinion disengage during linear travel of the rack relative to the pinion in a first direction, contact between the cam and follower cause the relative motion of the rack and pinion to continue in the first direction despite the disengagement of the teeth.

16. A surgical system comprising:
a drive unit on a support, the drive unit comprising a plurality of actuators and a plurality of output elements, each drive unit operable to linearly translate a corresponding one of the output elements;
a first surgical device comprising
an elongate shaft having a distal articulation section, and a plurality of actuation elements extending through the shaft,
an input subsystem carried at a proximal end of the shaft, the input subsystem including a plurality of first input elements each operatively associated with a corresponding one of the actuation elements, each input element linearly translatable relative to the elongate shaft;
wherein the surgical device is removably mounted relative to the drive unit to position a first plurality of output elements in drive relationships with corresponding input elements;
wherein operation of an actuator linearly translates an output element, causing linear translation of a corresponding input element and engagement of an actuation member;
a second surgical device having a second shaft, the second surgical instrument further comprising a second input subsystem carried at a proximal end of the second shaft, at least one second actuation element for causing motion of a portion of the second surgical device, the second input subsystem including a plurality of second input elements each operatively associated with a corresponding one of the second actuation elements, each second input element linearly translatable relative to the second shaft;
wherein the second surgical device is removably mountable to position a second plurality of output elements in a drive relationship with corresponding second input elements, wherein the plurality of first input elements and the plurality of second input elements are not identical to one another.

17. The system of claim 15, wherein output elements that are positioned to actuate a first function of the first instrument when it is positioned to be driven by the drive unit are positioned to actuation a second, different, function of the second instrument when the second instrument is positioned to be driven by the drive unit.

18. A surgical system comprising:
a drive unit on a support, the drive unit comprising a plurality of actuators and a plurality of output elements, each drive unit operable to linearly translate a corresponding one of the output elements;
a first surgical device comprising
an elongate tubular shaft having a distal articulation section, and a plurality of actuation elements extending through the shaft,
an input subsystem carried at a proximal end of the shaft, the input subsystem including a plurality of input elements each operatively associated with a corresponding one of the actuation elements, each input element linearly translatable relative to the elongate shaft;
wherein the surgical device is removably mounted relative to the drive unit to position a first plurality of output elements in drive relationships with corresponding input elements;
wherein operation of an actuator linearly translates an output element, causing linear translation of a corresponding input element and engagement of an actuation member;
the system further including an auxiliary device having second input elements, each operatively associated with an actuation element for a function of the auxiliary device, wherein the auxiliary device is removably mounted relative to the drive unit to position a second plurality of output elements in a drive relationships with corresponding second input elements, the first plurality different from the second plurality, the drive unit configured to allow the surgical device and auxiliary device to be driven by the drive unit at the same time.

* * * * *